(12) United States Patent
Ammendola et al.

(10) Patent No.: US 7,338,969 B2
(45) Date of Patent: Mar. 4, 2008

(54) MODULATION OF PATHOGENICITY

(75) Inventors: Aldo Ammendola, München (DE); Katharina Aulinger-Fuchs, Neuried (DE); Astrid Gotschlich, München (DE); Bernd Kramer, Aachen (DE); Martin Lang, Gräfelfing (DE); Wael Saeb, Planegg-Martinsried (DE); Udo Sinks, München (DE); Andreas Wuzik, Untermeitingen (DE)

(73) Assignee: Quonova, LLC, Melbourne, FL (US)

( * ) Notice: Subject to any disclaimer, the term of this patent is extended or adjusted under 35 U.S.C. 154(b) by 381 days.

(21) Appl. No.: 10/839,221

(22) Filed: May 6, 2004

(65) Prior Publication Data
US 2004/0235914 A1 Nov. 25, 2004

Related U.S. Application Data

(63) Continuation-in-part of application No. 10/429,875, filed on May 6, 2003, which is a continuation-in-part of application No. 10/094,301, filed on Mar. 8, 2002, now abandoned.

(30) Foreign Application Priority Data
May 6, 2003 (EP) .................. 03010185

(51) Int. Cl.
A01N 43/78 (2006.01)
A61K 31/425 (2006.01)

(52) U.S. Cl. .................. 514/365; 514/372; 514/374

(58) Field of Classification Search ............... 514/365, 514/372, 374, 340
See application file for complete search history.

(56) References Cited

U.S. PATENT DOCUMENTS

| | | | | |
|---|---|---|---|---|
| 3,265,506 A | * | 8/1966 | Weissberger et al. | ....... 430/556 |
| 4,069,252 A | | 1/1978 | Findeisen | |
| 4,146,454 A | | 3/1979 | Haber | |
| 4,436,479 A | | 3/1984 | Belloli | |
| 5,155,011 A | | 10/1992 | Zertani | |
| 5,190,928 A | | 3/1993 | Schurter | |
| 5,395,730 A | | 3/1995 | Podszun | |
| 5,523,311 A | | 6/1996 | Schurter | |
| 5,585,473 A | | 12/1996 | Bendiak | |
| 5,612,359 A | | 3/1997 | Murugesan | |
| 5,846,990 A | | 12/1998 | Murugesan | |
| 5,990,109 A | | 11/1999 | Chen | |
| 6,159,980 A | | 12/2000 | Arvanitis | |
| 6,300,352 B1 | | 10/2001 | Cheshire | |
| 6,395,282 B1 | | 5/2002 | Kende et al. | |
| 6,399,773 B1 | | 6/2002 | Liu | |
| 6,476,042 B1 | | 11/2002 | Harrison | |
| 6,555,540 B1 | | 4/2003 | Mylari | |
| 6,815,528 B2 | | 11/2004 | Wang | |
| 6,858,627 B2 | | 2/2005 | Bekkali | |
| 6,894,111 B2 | | 5/2005 | Wang | |
| 2004/0019117 A1 | | 1/2004 | Protopopova | |
| 2004/0033986 A1 | | 2/2004 | Protopopova | |
| 2006/0073667 A1 | | 4/2006 | Li | |

FOREIGN PATENT DOCUMENTS

| | | |
|---|---|---|
| DE | 101 18 310 | * 10/2002 |
| EP | 0 525 686 | 2/1993 |
| EP | 0 540 472 | 5/1993 |
| EP | 0 638 545 | 2/1995 |
| EP | 0 982 292 | 3/2000 |
| FR | 1 439 334 | 4/1966 |
| GB | 2 331 299 | 5/1999 |
| JP | 3-232849 | 10/1991 |
| WO | 95/01175 | 1/1995 |
| WO | WO 95/24403 | 9/1995 |
| WO | 96/29392 | 9/1996 |
| WO | 98/57618 | 12/1998 |
| WO | 98/58075 | 12/1998 |
| WO | WO 98/57618 | 12/1998 |
| WO | WO 99/27786 | 6/1999 |
| WO | 99/53915 | 10/1999 |
| WO | 99/55368 | 11/1999 |
| WO | 01/26650 | 4/2001 |
| WO | 01/51456 | 7/2001 |

(Continued)

OTHER PUBLICATIONS

Hentzer, M., et al. Microbiology 2002, 148, 87-102.*

(Continued)

Primary Examiner—Sreeni Padmanabhan
Assistant Examiner—Umamaheswari Ramachandran
(74) Attorney, Agent, or Firm—Womble Carlyle Sandridge & Rice, PLLC

(57) ABSTRACT

The present invention relates to the use of compounds of the general Formula (XIII):

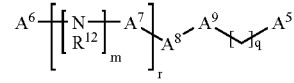

Figure 1:
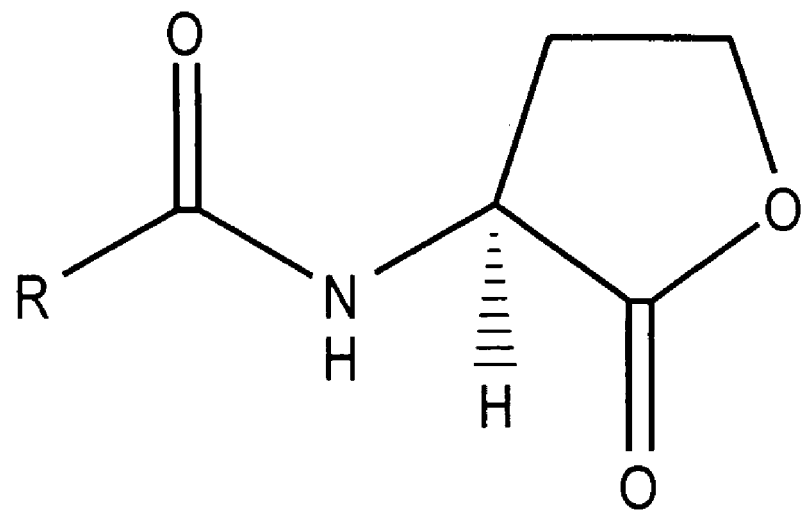

wherein
$A^7$ is C=O, C=S, $SO_2$, CH—$OR^{13}$, C=$NR^{12}$, or $CH_2$—$CHOR^{13}$;
$A^8$ is $C(R^{14})_2$, O, S, or $NR^{12}$;
$A^9$ is C=O, C=S, $SO_2$, CH—$OR^{13}$, C=$NR^{12}$, or $CH_2$—$CHOR^{13}$;
m is 0, or 1
q is 0, or 1
r is 0, or 1
$R^{12}$ is H, $CH_3$, $CH_2$—$CH_3$, $C_6H_5$, $OCH_3$, $OCH_2$—$CH_3$, OH, or SH;
$R^{13}$ is H, $CH_3$, or $CH_2$—$CH_3$;
$R^{14}$ is H, alkyl, alkoxy, OH, or SH.

8 Claims, 1 Drawing Sheet

FOREIGN PATENT DOCUMENTS

| | | | |
|---|---|---|---|
| WO | WO 01/90090 | * | 11/2001 |
| WO | 02/088298 | | 11/2002 |
| WO | 03/004017 | | 1/2003 |
| WO | WO/03/015778 | | 2/2003 |
| WO | 03/022828 | | 3/2003 |
| WO | 03/026641 | | 4/2003 |
| WO | WO 03/039529 | | 5/2003 |
| WO | WO 03/039549 | | 5/2003 |

OTHER PUBLICATIONS

Patent Abstracts of Japan, JP 59-210440, Nov. 29, 1984.

C. S. Pak, et al., Synthesis, vol. 12, XP-001154580, pp. 1213-1214, "Aminolysis of 5-Acyl-2,2-Dimethyl-1,3-Dioxane-4,6-Diones (Acyl Meldrum's Acids) as a Versatile Method for the Synthesis of β-Oxo Carboxamides", Dec. 1992.

K. M. Smith, et al., Chemistry & Biology, vol. 10, No. 1, XP-002254860, pp. 81-89, "Induction and Inhibition of *Pseudomonas aeruginosa* Quorum Sensing by Synthetic Autoinducer Analogs", Jan. 2003.

Fuqua, C., et al., "Census and Consensus in Bacterial Ecosystems: The LuxR-LuxI Family of Quorum-Sensing Transcriptional Regulators," Anne. Rev. Microbiol. 50, pp. 727-751, 1996.

Eberl, L., "N-Acyl Homoserinelactone-mediated Gene Regulation in Gram-negative Bacteria," System Appl. Microbiol. 22, pp. 493-506, 1999.

De Kievit, T., et al., "Bacterial Quorum Sensing in Pathogenic Relationships," Infection and Immunity, pp. 4839-4849, Sep. 2000.

Davies, D. G., et al., "The Involvement of Cell-to-Cell Signals in the Development of a Bacterial Biofilm," Science, vol. 280, pp. 295-298, Apr. 10, 1998.

Huber, B., et al., "The cep quorum-sensing system of *Burkholderia cepacia* H111 controls biofilm formation and swarming motility," Microbiology, 147, pp. 2517-2528, 2001.

Costerton, J. W., et al., "Microbial Biofilms," Ann. Rev. Microbiol.

Govan, J. R. W., et al., "Microbial Pathogenesis in Cystic Fibrosis: Mucoid *Pseudomonas aeruginosa* and *Burkholderia cepacia*," Microbiological Reviews, Sep. 1996, pp. 539-574.

Costerton, J. W., et al., "Bacterial Biofilms: A Common Cause of Persistent Infections," Science, vol. 284, May 21, 1999, pp. 1318-1322.

Lewis, K., "Riddle of Biofilm Resistance," Antimicrobial Agents and Chemotherapy, Apr. 2000, pp. 999-1007.

Govan, J. R. W., "*Burkholderia cepacia:* medical, taxonomic and ecological issues," J. Med. Microbiol. 45, pp. 395-407, 1996.

Chhabra, S. R., et al., "Synthetic Analogues of the Bacterial Signal (Quorum Sensing) Molecule N-(3-Oxododecanoyl)-L-homoserine Lactone as Immune Modulators," J. Med. Chem. 2003, 46, pp. 97-104.

Stickler, D. J., et al., "Biofilms on Indwelling Urethral Catheters Produce Quorum-Sensing Molecules in Situ and In Vitro," Applied and Environmental Microbiology, Sep. 1998, pp. 3486-3490.

Dong, Y. H., et al., "Quenching quorum-sensing-dependent bacterial infection by an N-acyl homoserine lactonase," Nature, vol. 411, Jun. 14, 2001, pp. 813-817.

Schaefer, A. L., et al., "Quorum Sensing in *Vibrio fischeri*; Probing Autoinducer-LuxR Interactions with Autoinducer Analogs," Journal of Bacteriology, May 1996, pp. 2897-2901.

Zhu j., et al., "Anagogs of Autoinducer 3-Oxooctanoyl-Homoserine Lactone Strongly Inhibit Activity of the TraR Protein of *Agrobacterium tumefaciens,*" Journal Bacteriology, Oct. 1998, pp. 5398-5405.

McClean, K. H., et al., "Quorum sensing and *Chromobacterium violaceum:* exploitation of violacein production and inhibition for the detection of N-acelhomoserine lactones," Microbiology 143, 1997, 3703-3711.

Swift S., et al., "Quorum Sensing in *Aeromonas hydrophila* and *Aeromonas salmonicida:* Identification of the LuxRI Homologs AhyRI and AsaRI and Their Cognate N-Acylhomoserine Lactone Signal Molecules," Journal of Bacteriology, Sep. 1997, pp. 5271-5281.

Pesci, E. C., et al., "Regulation of las and rhl Quorum Sensing in *Pseudomonas aeruginosa,*" Journal of Bacteriology, May 1997, pp. 3127-3132.

Hentzer, M., et al., "Inhibition of quorum sensing in *Pseudomonas aeruginosa* biofilm bacteria by a halogenated furonone compound," Microbiology, 148, 2002, pp. 87-102.

Smith, K. M., et al., "Library Screening for Synthetic Agonists and Antagonists of a *Pseudomonas aeruginosa* Autoinducer," Chemistry & Biology, vol. 10, pp. 563-571, Jun. 2003.

Fuqua, W. C., et al., "Quorum Sensing in Bacteria: the LuxR-LuxI Family of Cell Density-Responsive Transcriptional Regulators," Journal of Bacteriology, Jan. 1994, pp. 269-275.

Oikawa, Y., et al., "Methyl Phenylacetylacetate from Phenylacetyl Chloride and Meldrum's Acid,"Organic Syntheses, CV 7, pp. 359-360.

Oikawa, Y., et al., "Meldrum's Acid in Organic Synthesis 2. A General and Versatile Synthesis of β-Keto Esters," J. Org. Chem., vol. 43, No. 10, pp. 2087-2088, 1978.

Nakahata, M., et al., "The Preparation of Optically Pure 3-Hydroxyalkanoic Acid. The Enantioface-differentiating Hydrogenation of the C=O Double Bond with Modified Raney Nickel. XXXVII," Bull. Chem. Soc. Jpn, 55, pp. 2186-2189, 1982.

Matsuo, K., "Structure-Activity Relationships in Tetramic Acids and Their Copper (II) Complexes," Chem. Pharm. Bull. 28, pp. 2494-2502, 1980.

Monti, L., et al., "Sulla preparazione delle α-ossi-γ-metil-chinoline," Gass. Chim. Ital. 66, pp. 723-731, 1936.

Dekhane, M., et al., "A Novel Convenient Rout to the Naturally Occurring 3-Oxoacyl-L-Homoserinelactones and Related Bacterial Autoinducers," Tetrahedron Letters, vol. 37, No. 11, pp. 1883-1884, 1996.

Augelli-Szafran, C., et al., "Inhibitors of Acyl-CoA: Cholesterol Acyltransferase. 5. Identification and Structure-Activity Relationships of Novel β-Ketoamides as Hypocholesterolemic Agents," J. Med. Chem., 36, pp. 2943-2949, 1993.

Rowley, M., et al., "3-Acyl-4-hydroxyquinolin-2(1H)-ones. Systemically Active Anticonvulsants Acts by Antagonism at the Glycine Site of the N-Methyl-D-Aspartate Recepto Compound," J. Med. Chem. 1993, 36, pp. 3386-3396.

Sato, M., et al., "Synthesis of β-Ketocarboxamide Derivatives Using 2,2-Dimethyl-2H,4H-1,3-dioxin-4-ones," Chen. Pharm. Bull., vol. 32, No. 10, pp. 3848-3856, 1984.

Brennan, C. J., et al., "Synthetic Studies Towards the Group A Streptogramin Antibiotics. Synthesis of the C9-C23 Fragment," Tetrahedron Letters, 42, 2001, pp. 5195-5197.

Singer, R. A., "Catalytic, Enantioselective Dienolate Additions to Aldehydes: Preparation of Optically Active Acetoacetate Aldol Adducts," J. Am. Chem. Soc., 117, 1995, pp. 12360-12361.

Zirvi, K. A., et al., "Synthesis and Neuropharmacology of Butyrylureas," Synthesis and Neuropharmacology of Butyrylureas, Formaco Ed. Sci., 37, pp. 335-342, 1982.

Lin, W. O., et al., "Phenylenedioxydiacetamide End Group Effect," Monatsh. Chemie, 112, pp. 871-874, 1981.

Lin, W. O., et al., "Neutral Diamide Ionophores Phenylenediocydiacetamides," Monatsh. Chemie, 113, pp. 101-109, 1982.

Padwa, A., et al., "Rhodium(II)-Catalyzed Equilibration of Push-Pull Carbonyl and Ammonium Ylides. A Computationally Based Understanding of the Reaction Pathway," J. Am. Soc., 122, 2000, pp. 8155-8167.

Belletire, J. L., et al., "Exploratory Synthetic Methodology Involving the Acylureas," Synthetic Communications, 19(20), pp. 3543-3551, 1989.

O'Toole, G. A., et al., "Initiation of biofilm formation in *Pseudomonas fluorescens* WCS365 proceeds via multiple, convergent signaling pathways: a genetic analysis," Molecular Microbiology, 28(3), 1998, pp. 449-461.

Pratt, L. A., et al., "Genetic analysis of *Escherichia coli* biofilm formation: role of flagella, motility, chemotaxis and type I pili," Molecular Microbiology, 30(2), 1998, pp. 285-293.

Römling, U., et al., "Epidemiology of Chronic *Pseudomonas aeruginosa* Infections in Cystic Fibrosis," J. Infectious Diseases, 1994, 170, pp. 1616-1621.

Gotschlich, A., et al., "Synthesis of Multiple N-Acylhomoserine Lactones is Wide-spread Among Members of the *Burkholderia cepacia* Comples," System Appl. Microbiol. 24, pp. 1-14, 2001.

Clark, D. J., et al., "DNA Replication and the Division Cycle in *Escherichia coli*," J. Mol. Biol., 23, 1967, pp. 99-112.

* cited by examiner

MODULATION OF PATHOGENICITY

This application is a continuation-in-part of U.S. application Ser. No. 10/429,875, filed May 6, 2003, which is a continuation-in-part of U.S. application Ser. No. 10/094,301, filed Mar. 8, 2002 now abandoned.

The present invention relates to the use of compounds such as amide, carbazide and hydrazide derivatives as selective inhibitors of bacterial pathogens. In particular the invention refers to a family of compounds that block the quorum sensing system of Gram-negative bacteria, a process for their manufacture, pharmaceutical compositions containing them and to their use for the treatment and prevention of microbial damages and diseases, in particular for diseases where there is an advantage in inhibiting quorum sensing regulated phenotypes of pathogens.

Many microorganisms, including bacteria, fungi, protozoa and algae cause severe damages or diseases in different areas such as industry, agriculture, environment and medicine. Especially bacteria as human pathogens cause tremendous costs in public health systems worldwide. The continuing emergence of multiple-drug-resistant bacterial strains has necessitated finding new compounds that can be used in antibacterial treatment. There are two broad strategies for the control of bacterial infection: either to kill the organism or to attenuate its virulence such that it fails to adapt to the host environment. The latter approach has, however, lacked specific targets for rational drug design. The discovery that Gram-negative bacteria employ a signal transduction pathway comprising a small molecule to globally regulate the production of virulence determinants offers such a novel target.

A wide variety of Gram-negative bacteria produce N-acyl-L-homoserine lactone (AHL or HSL, FIG. 1) derivatives as signal molecules in intercellular communication. These molecules, also referred to as "pheromones" or "quoromones", comprise a homoserine lactone moiety linked to an acyl side chain. Bacteria use this signaling system to monitor their population cell density in a process referred to as "quorum sensing". In each cell of a population an HSL synthase from usually the LuxI family of proteins produce a low basal level of diffusible HSLs. The HSL concentration increases with bacterial population density until a threshold concentration is reached which results in expression of various HSL-dependent genes through an HSL-receptor protein belonging generally to the LuxR family of transcriptional regulators. This HSL-receptor protein complex serves not only as positive transcription regulator of quorum sensing regulated genes but also as positive regulator for the HSL synthesis itself. Therefore, the entire system is amplified via a process of autoinduction.

This system was first discovered in the bioluminescent marine bacteria *Vibrio harveyi* and *V. fischeri* where it is used to control bioluminescence expression. In recent years it has become apparent that many Gram-negative bacteria employ one or more quorum sensing systems comprising HSL derivatives with different acyl side chains to regulate in a cell-density dependent manner a wide variety of physiological processes such as swarming motility, biofilm formation, pathogenicity, conjugation, bioluminescence or production of pigments and antibiotics (Table 1, for reviews and further references see, e.g.: Fuqua et al., *Ann. Rev. Microbiol.* 50:727-51, 1996: Fuqua & Greenberg, *Curr. Opinion Microbiol.* 1:183-89, 1998; Eberl, *Syst. Appl. Microbiol.* 22:493-506, 1999; De Kievit & Iglewski, *Infect. Immun.* 68:4839-49, 2000).

TABLE 1

Summary of HSL-based quorum sensing systems

| Bacterium | Regulatory proteins | Major HSL | HSL-regulated phenotype |
|---|---|---|---|
| *Aeromonas hydrophila* | AhyR, AhyI | C4-HSL | Extracellular protease, biofilm formation |
| *Aeromonas salmonicida* | AsaR, AsaI | C4-HSL | Extracellular protease |
| *Agrobacterium tumefaciens* | TraR, TraI | 3-oxo-C8-HSL | Conjugal transfer |
| *Burkholderia cepacia* | CepR, CepI | C8-HSL | Protease, lipase, ornibactin synthesis, biofilm formation, swarming motility |
| *Chromobacterium violoceum* | CviR, CviI | C6-HSL | Antibiotics, violacein, exoenzymes, cyanide |
| *Enterobacter agglomerans* | EagR, EagI | 3-oxo-C6-HSL | Unknown |
| *Erwinia carotovora* | CarR, (CarI) ExpR, ExpI | 3-oxo-C6-HSL | Carbapenem antibiotics, exoenzyme production |
| *Erwinia chrysanthemi* | ExpR, ExpI (EchR, EchI) | 3-oxo-C6-HSL | Pectinase expression |
| *Escherichia coli* | SdiA | Unknown | Cell division, virulence factor production |
| *Nitrosomonas europaea* | Unknown | 3-oxo-C6-HSL | Emergence from lag phase |
| *Obesumbacterium proteus* | OprR, OprI | 3-oxo-C6-HSL | Unknown |
| *Panloea stewartii* | EsaR, EsaI | 3-oxo-C6-HSL | Exopolysaccharide production, virulence factor production |
| *Pseudomonas aeruginosa* | LasR, LasI | 3-oxo-C12-HSL | Extracellular virulence factors, Xcp, biofilm formation, RpoS, RblR |
| *Pseudomonas aeruginosa* | RhlR, RhlI | C4-HSL | Extracellular virulence factors, cyanide, lectins, pyocyanin, rhamnolipid, type 4 pili, twitching motility |

TABLE 1-continued

Summary of HSL-based quorum sensing systems

| Bacterium | Regulatory proteins | Major HSL | HSL-regulated phenotype |
|---|---|---|---|
| Pseudomonas aureofaciens | PhzR, PhzI | C6-HSL | Phenazine antibiotics |
| Pseudomonas fluorescens | HdtS | 3-hydroxy-7-cis-C14-HSL | Unknown |
| Ralstonia solanacearum | SolR, SolI | CS-HSL | Unknown |
| Rhizobium etli | RaiR, RaiI | 7 HSLs | Root nodulation |
| Rhizobium leguminosarum | RhiR | 3-hydroxy-7-cis-C14-HSL | Nodulation, bacteriocin, stationary phase survival |
| Rhizobium leguminosarum | RhiR, RhiI | C6-HSL, C8-HSL | rhizome interactions |
| Rhodobacter sphaeroides | CerR, CerI | 7-cis-C14-HSL | Clumping factor |
| Serratia liquefaciens | SwrR, SwrI | C4-HSL | Swarming motility, protease, serrawettin W2, lipase |
| Vibrio anguillarum | VanR, VanI | 3-oxo-C10-HSL | Unknown |
| Vibrio anguillarum | VanM, VanN | C6-HSL, 3-hydroxy-C6-HSL | Unknown |
| Vibrio fischeri | LuxR, LuxI | 3-oxo-C6-HSL | Bioluminescence |
| Vibrio harveyi | LuxM, LuxN | 3-hydroxy-C4-HSL | Bioluminescence, PHB synthesis |
| Xenorhabdus nematophilus | Unknown | 3-hydroxy-C4-HSL | Virulence |
| Yersinia enterocolitica | YenR, YenI | C6-HSL, 3-oxo-C6-HSL | Unknown |
| Yersinia pestis | YpeR, YpeI | Unknown | Unknown |
| Yersinia pseudotuberculosis | YpsR, YpsI | 3-oxo-C6-HSL | Motility, clumping |
| Yersinia pseudotuberculosis | YtbR, YtbI | C8-HSL | Unknown |
| Yersinia ruckeri | YukR, YukI | Unknown | Unknown |

With regard to bacteria that utilize HSL-based quorum sensing as part of their lifestyle, *Pseudomonas aeruginosa* is perhaps the best understood in terms of the role quorum sensing plays in pathogenicity. In this human opportunistic pathogen, which causes nosocomial infections in immuno-compromized patients and has an extremely high potential to develop resistance mechanisms against traditional antibiotic treatment, production of many virulence factors including expression of alkaline protease, endoproteinase, LasA protease, LasB elastase, anthranilate synthase, hemolysins, lectin, cytochrome c oxidase, catalase, Mn- and Fe-dependent superoxide dismutases, exotoxin A, exoenzyme S, chitinase, chitin binding protein, phenazine, hydrogen cyanide, pyocyanin, pyoverdine, phospholipase C, rhamnolipids, sigma factor S, components of the protein secretion apparatus, efflux transporters, production of alginate and adhesins, twitching motility and pilin export is regulated by two interlinked quorum sensing circuits. Moreover, it has been demonstrated that this signaling system is involved in the ability of *P. aeruginosa* to form biofilms (Davies et al., *Science* 280:295-8, 1998). Recently Huber et al. (*Microbiology* 147:2517-28, 2001) demonstrated that biofilm formation and swarming motility of *Burkholderia cepacia*, like *P. aeruginosa* a human opportunistic pathogen, is also dependent on an HSL-based quorum sensing system.

Biofilms are defined as an association of microorganisms growing attached to a surface and producing a slime layer of extracellular polymers in which the microbial consortia is embedded in a protective environment (for a review see: Costerton et al., *Ann. Rev. Microbiol.* 49:711-45, 1995). Biofilms represent a severe problem as bacteria integrated in such a polymer matrix develop resistance to conventional antimicrobial agents. *P. aeruginosa* cells, for example, growing in an alginate slime matrix have been demonstrated to be resistant to antibiotics (e.g., aminoglycosides, β-lactam antibiotics, fluoroquinolones) and disinfectants (Govan & Deretic, *Microbiol. Rev.* 60:539-74, 1996). Several mechanisms for biofilm-mediated resistance development have been proposed (Costerton et al., *Science* 284:1318-22, 1999).

In most natural, clinical and industrial settings bacteria are predominantly found in biofilms. Drinking water pipes, ship hulls, teeth or medical devices represent typical surfaces colonized by bacteria. On the one hand biofilms decrease the life time of materials through corrosive action in the industrial field, a process also referred to as "biofouling". Furthermore, microbial biofilms growing for example on ship hulls increase fuel consumption through enhanced frictional resistance and simultaneously reduce maneuverability. On the other hand two thirds of all bacterial infections in humans are associated with biofilms (Lewis, *Antimicrob. Agents Chemother.* 45-999-1007, 2001).

*Pseudomonas aeruginosa*, for example, forms infectious biofilms on surfaces as diverse as cystic fibrosis lung tissue, contact lenses, and catheter tubes (Stickler et al., *Appl. Environm. Microbiol.* 64:3486-90, 1998). *Burkholderia cepacia* also forms biofilms in lungs of cystic fibrosis patients and is a major industrial contaminant (Govan et al., *J. Med. Microbiol.* 45:395-407, 1996). Since biofilm formation of both organisms is demonstrated to require an HSL signaling system, inhibition of their quorum sensing systems would result in an impaired ability to form biofilms and therefore in an increased susceptability to antibacterial treatment.

Beside the role of HSL derivatives as signaling molecules of bacterial cell-to-cell communication it bas been demonstrated that HSL interfere also with higher organisms. Since HSL derivatives inhibit murine and human leucocyte proliferation and TNF-alpha secretion by lipopolysaccharide (LPS) stimulated human leucocytes (Chhabra et al., *J. Med.*

Chem. 46:97-104, 2003), the suitability of these compounds for immunological diseases, particularly autoimmune diseases such as psoriasis, rheumatoid arthritis, multiple sclerosis and type I (autoimmune) diabetes is indicated (WO 03/004017, WO 03/022828).

Furthermore, certain HSL molecules are capable of reducing the heart beat without substantially reducing arterial blood pressure. These compounds and analogs of them could, therefore, be suitable for the treatment of cardiac tachyarrhythmias, ischaemic heart disease, congestive heart failure (WO 01/26650). Additionally, HSL compounds have been reported as possible antiallergic drug (WO 95/01175) and for the treatment of a range of diseases including cancer, breast cancer, obesity, lipid metabolism disorders, immune disease, immune deficiency or immune disorders by modulationg STAT activity (WO 03/026641).

The discovery that a wide spectrum of bacterial organisms use quorum sensing to control virulence factor production and other phenotypes such as biofilm formation makes it an attractive target for antimicrobial therapy. Pathogenic organisms using this signaling system to control virulence could potentially be rendered avirulent by blocking this cell-cell communication system. In contrast to traditional antibiotics, the risk of resistance development seems to be very low, since quorum sensing blocking agents would not kill the organism but disturb signal transduction pathways. There are several possibilities of interrupting the quorum sensing circuit.

For example, plants expressing an HSL-lactonase enzyme originally derived from *Bacillus* sp. have been demonstrated to quench pathogen quorum sensing signaling and to significantly enhance resistance to *Erwinia carotovora* infections (Dong et al., *Nature* 411:813-7, 2001). An alternative way to block cell signaling could be to interrupt the HSL synthesis by using analogs of HSL precursors.

However, the most promising possibility to block quorum sensing is to take advantage of the unique specificity the HSLs and HSL-receptor proteins show for one another. The ability of homoserine lactone-based analogs to inhibit activation of HSL-receptor proteins has already been demonstrated in a number of bacteria including *Vibrio fischeri* (Schaefer et al., *J. Bacteriol.* 178:2897-901, 1996), *Agrobacterium tumefaciens* (Zhu et al., *J. Bacteriol.* 180:5398-405, 1998), *Chromobacterium violaceum* (McLean et al., *Microbiology* 143:3703-11, 1997), *Aeromonas salmonicida* (Swift et al., *J. Bacteriol.* 179:5271-81, 1997) and *Pseudomonas aeruginosa* (Pesci et al., *J. Bacteriol.* 179: 3127-32, 1997). However, none of these compounds have been developed as antimicrobial agents, e.g. in medical therapy, so far.

The are only few non-HSL-based antimicrobials described which are supposed to interfere specifically with HSL-regulated processes, for example halogenated furanone derivatives which are structurally similar to HSLs and have been isolated from red marine algae *Delisea pulchra* (WO 96/29392; Hentzer et al., *Microbiology* 148:87-102, 2002). Additionally, these substances have been demonstrated to inhibit also Gram-positive bacteria (WO 99/53915). However, the use of most of these furanone compounds is limited due to toxicity making them unsuitable for veterinary and medical applications.

Futhermore, Smith et al. (*Chem. Biol.* 10:81-9, 2003; *Chem. Biol.* 10:563-71, 2003) recently published *Pseudomonas aeruginosa* HSL analogs with slight structural variations targeted to the HSL moiety which act both as quorum sensing agonists and antagonists. Additionally, WO 02/088298 reportedly provides certain nitrogen heterocyclic molecules for controlling biofilms based on the interference with quorum sensing.

Many target genes involved in biofilm formation, methods of screening for compounds to control biofilm development and HSL-based compositions to prevent biofilm formation have been described (WO 99/55368, WO 98/57618, WO 99/27786, WO 98/58075), but until now no promising antibacterial drug candidate has been developed that is capable of inhibiting virulence gene expression and biofilm formation in different areas, preferentially in the medical field.

It is an object of the present invention to provide compounds blocking specifically quorum sensing regulated processes without inhibiting bacterial growth. Furthermore, these compounds should not be structural derivatives of the homoserine lactone family of regulatory compounds and should not exhibit any toxic properties.

Accordingly, we have been able to find compounds that can significantly reduce virulence gene expression and biofilm formation of several human pathogens. In contrast to the furanones the compounds of this invention do not show any toxic effect and are therefore suitable for applications in a wide area. Such applications could be the use of the compounds for instance as new antibiotic therapeutics, disinfectants, antifouling coatings or coatings of medical devices. In contrast to traditional antibacterial agents (like amide or 1,2-acylhydrazine derivatives in WO 01/51456; for the synthesis of amide or 1,2-acylhydrazine derivatives see also EP 638545 and EP 982292), the compounds of the present invention do not kill the microorganisms, but render them avirulent. The advantage of this alternative strategy is that the emergence of bacterial resistance against such antimicrobials is extremely improbable.

In general, the present invention provides compounds selectively modulating bacterial cell-cell communication. Through inhibition of this communication system the expression of many HSL-dependent virulence genes and other phenotypes like swarming motility and biofilm formation are significantly reduced or completely abolished rendering a bacterial population more susceptible to the host immune-response or to treatment with traditional antibacterial agents.

Thus, in one aspect, the invention refers to a method for inhibiting an HSL-regulated process in a microorganism by exposing the microorganism to a new class of compounds with an inhibitory effect on bacterial signaling.

The present invention is directed to novel compounds of the general Formula (I) and pharmaceutically acceptable salts thereof:

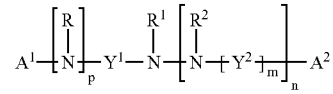

wherein

R is H, alkyl, cycloalkyl, aryl or heteroaryl;

$R^1$ is alkyl, cycloalkyl, aryl or heteroaryl;

$R^2$ is H, alkyl, cycloalkyl, aryl or heteroaryl;

$A^1$ is a substituted monocyclic aromatic ring system;

$A^2$ is an optionally substituted $C_1$-$C_{20}$-alkyl group which may contain one or more group(s) Z;

Z is selected from the group consisting of S, O, N, $NR^4$, CO, $CO_2$, CS, SO or SO;

X is selected from the group consisting of S, O, N, $NR^4$, SO or $SO_2$;

said substituted ring system carries a substituent $R^3$ on one or more of the carbon atoms of said ring system;

said substituted $C_1$-$C_{20}$-alkyl group carries a substituent $R^3$ on one or more of the carbon atoms of said alkyl group;

$R^3$ is independently H, $OR^4$, $SR^4$, hydroxyalkyl, hydroxyalkylamine, cycloalkyl, halogen, haloalkyl, haloalkyloxy, $NO_2$, CN, $SO_2NR^4R^5$, $CO_2NR^4R^5$, $COR^4$, $CO_2R^4$, $SO_2R^4$, $SO_3R^4$, $NR^4R^5$, alkyl, aryl or heteroaryl;

$R^4$ is H, alkyl, cycloalkyl, aryl or heteroaryl;

$R^5$ is H, O-alkyl, O-aryl, alkyl, heteroaryl or aryl;

$Y^1$ and $Y^2$ are independent from each other C=O;

p is 0, m is 0, and n is 0;

an alkyl group, if not stated otherwise, denotes a linear or branched $C_1$-$C_6$-alkyl, preferably a linear or branched chain of one to five carbon atoms, a linear or branched $C_1$-$C_6$-alkenyl or a linear or branched $C_1$-$C_6$-alkinyl group, which can optionally be substituted by one or more substituents $R^3$, preferably by halogen;

the $C_1$-$C_6$-alkyl, $C_1$-$C_6$-alkenyl and $C_1$-$C_6$-alkinyl residue may be selected from the group comprising —$CH_3$, —$C_2H_5$, —CH=$CH_2$, —C≡CH, —$C_3H_7$, —CH($CH_3$)$_2$, —$CH_2$—CH=$CH_2$, —C($CH_3$)=$CH_2$, —CH=CH—$CH_3$, —C≡C—$CH_3$, —$CH_2$—C≡CH, —$C_4H_9$, —$CH_2$CH($CH_3$)$_2$, —CH($CH_3$)—$C_2H_5$, —C($CH_3$)$_3$, —$C_5H_{11}$, —$C_6H_{13}$, —C($R^3$)$_3$, —$CR^3(R^{3'})_2$, —$CR^3(R^{3'})R^{3''}$, —$C_2(R^3)_5$, —$CH_2$—C($R^3$)$_3$, —$CH_2$—$CR^3(R^{3'})_2$, —$CH_2$—$CR^3(R^{3'})R^{3''}$, —$C_3(R^3)_7$, —$C_2H_4$—C($R^3$)$_3$, —$C_2H_4$—CH=$CH_2$, —CH=CH—$C_2H_5$, —CH=C($CH_3$)$_2$, —$CH_2$—CH=CH—$CH_3$, —CH=CH—CH=$CH_2$, —$C_2H_4$—C≡CH, —C≡$C_2H_5$, —$CH_2$—C≡C—$CH_3$, —C≡C—CH=$CH_2$, —CH=CH—C≡CH, —C≡C—C≡CH, —$C_2H_4$—CH($CH_3$)$_2$, —CH($CH_3$)—$C_3H_7$, —$CH_2$—CH($CH_3$)—$C_2H_5$, —CH($CH_3$)—CH($CH_3$)$_2$, —C($CH_3$)$_2$—$C_2H_5$, —$CH_2$—C($CH_3$)$_3$, —$C_3H_6$—CH=$CH_2$, —CH=CH—$C_3H_7$, —$C_2H_4$—CH=CH—$CH_3$, —$CH_2$—CH=CH—$C_2H_5$, —$CH_2$—CH=CH—CH=$CH_2$, —CH=CH—CH=CH—$CH_3$, —CH=CH—$CH_2$—CH=$CH_2$, —C($CH_3$)=CH—CH=$CH_2$, —CH=C($CH_3$)—CH=$CH_2$, —CH=CH—C($CH_3$)=$CH_2$, —$CH_2$—CH=C($CH_3$)$_2$, —C($CH_3$)=C($CH_3$)$_2$, —$C_3H_6$—C≡CH, —C≡C—$C_3H_7$, —$C_2H_4$—C≡$CH_3$, —$CH_2$—C≡C—$C_2H_5$, —$CH_2$—C≡C—CH=$CH_2$, —$CH_2$—CH=CH—C≡CH, —$CH_2$—C≡C—C≡CH, —C≡C—CH=CH—$CH_3$, —CH=CH—C≡C—$CH_3$, —C≡C—C≡C—$CH_3$, —C≡C—$CH_2$—CH=$CH_2$, —CH=CH—$CH_2$—C≡CH, —C≡C—$CH_2$—C≡CH, —C($CH_3$)=CH—CH=$CH_2$, —CH=C($CH_3$)—CH=$CH_2$, —CH=CH—C($CH_3$)=$CH_2$, —C($CH_3$)=CH—C≡CH, —CH=C($CH_3$)—C≡CH, —C≡C—C($CH_3$)=$CH_2$, —$C_3H_6$—CH($CH_3$)$_2$, —$C_2H_4$—CH($CH_3$)—$C_2H_5$, —CH($CH_3$)—$C_4H_9$, —$CH_2$—CH($CH_3$)—$C_3H_7$, —CH($CH_3$)—$CH_2$—CH($CH_3$)$_2$, —CH($CH_3$)—CH($CH_3$)—$C_2H_5$, —$CH_2$—CH($CH_3$)—CH($CH_3$)$_2$, —$CH_2$—C($CH_3$)$_2$-$C_2H_5$, —C($CH_3$)$_2$—$C_3H_7$, —C($CH_3$)$_2$-CH($CH_3$)$_2$, —$C_2H_4$—C($CH_3$)$_3$, —CH($CH_3$)—C($CH_3$)$_3$, —$C_4H_8$—CH=$CH_2$, —CH=CH—$C_4H_9$, —$C_3H_6$—CH=CH—$CH_3$, —$CH_2$—CH=CH—$C_3H_7$, —$C_2H_4$—CH=CH—$C_2H_5$, —$CH_2$—C($CH_3$)=C($CH_3$)$_2$, —$C_2H_4$—CH=C($CH_3$)$_2$, —$C_4H_8$—C≡CH, —C≡C—$C_4H_9$, —$C_3H_6$—C≡C—$CH_3$, —$CH_2$—C≡C—$C_3H_7$, —$C_2H_4$—C≡C—$C_2H_5$; $R^3$, $R^{3'}$ or $R^{3''}$ being as defined above;

a cycloalkyl group denotes a non-aromatic ring system containing three to eight carbon atoms, preferably four to eight carbon atoms, wherein one or more of the carbon atoms in the ring can be substituted by a group X, X being as defined above; the $C_3$-$C_8$-cycloalkyl residue may be selected from the group comprising -cyclo-$C_3H_5$, -cyclo-$C_4H_7$, -cyclo-$C_5H_9$, -cyclo-$C_6H_{11}$, -cyclo-$C_7H_{13}$, -cyclo-$C_8H_{15}$;

an alkoxy group denotes an O-alkyl group, the alkyl group being as defined above; the alkoxy group is preferably a methoxy, ethoxy, isopropoxy, t-butoxy or pentoxy group.

an haloalkyl group denotes an alkyl group which is substituted by one to five halogen atoms, the alkyl group being as defined above; the haloalkyl group is preferably a —C($R^{10}$)$_3$, —$CR^{10}(R^{10'})_2$, —$CR^{10}(R^{10'})R^{10''}$, —$C_2(R^{10})_5$, —$CH_2$—C($R^{10}$)$_3$, —$CH_2$—$CR^{10}(R^{10'})_2$, —$CH_2$—$CR^{10}(R^{10'})R^{10''}$, —$C_3(R^{10})_7$ or —$C_2H_4$—C($R^{10}$)$_3$, wherein $R^{10}$, $R^{10'}$, $R^{10''}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC($R^{10}$)$_3$, —$OCR^{10}(R^{10'})_2$, —$OCR^{10}(R^{10'})R^{10''}$, —$OC_2(R^{10})_5$, —$OCH_2$—C($R^{10}$)$_3$, —$OCH_2$—$CR^{10}(R^{10'})_2$, —$OCH_2$—$CR^{10}(R^{10'})R^{10''}$, —$OC_3(R^{10})_7$ or —$OC_2H_4$—C($R^{10}$)$_3$, wherein $R^{10}$, $R^{10'}$, $R^{10''}$ represent F, Cl, Br or I, preferably F;

a hydroxyalkylamino group denotes an (HO-alkyl)$_2$—N— group or HO-alkyl-NH— group, the alkyl group being as defined above;

a halogen group is chlorine, bromine, fluorine or iodine;

an aryl group preferably denotes an aromatic group having five to fifteen carbon atoms, which can optionally be substituted by one or more substituents $R^3$, where $R^3$ is as defined above; the aryl group is preferably a phenyl group, —$CH_2$—$C_6H_4$, —$C_2H_4$—$C_6H_4$, —CH=CH—$C_6H_4$, —C≡C—$C_6H_4$, -o-$C_6H_4$—$R^3$, -m-$C_6H_4$—$R^3$, -o-$CH_2$—$C_6H_4$—$R^3$, -m-$CH_2$—$C_6H_4$—$R^3$, -p-$CH_2$—$C_6H_4$—$R^3$;

a heteroaryl group denotes a 5- or 6-membered heterocyclic group which contains at least one heteroatom like O, N, S. This heterocyclic group can be fused to another ring. For example, this group can be selected from an oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4pyrimidinyl, 5-pyrimidinyl, 3-pyridazinyl, 4-pyridazinyl, 2-pyrazinyl, 1-pyrazolyl, 3-pyrazolyl, 4-pyrazolyl, indolyl, indolinyl, benzo-[b]-furanyl, benzo[b]thiophenyl, benzimidazolyl, benzothiazolyl, quinazolinyl, quinoxazolinyl, or preferably isoxazol-3-yl, isoxazol-4-yl, isoxazol-5-yl, quinolinyl, tetrahydroquinolinyl, isoquinolinyl, tetrahydroisoquinolinyl group. This heterocyclic group can optionally be substituted by one or more substituents $R^3$, where $R^3$ is as defined above.

for regulation of the quorum sensing system of microorganisms.

The present invention is also directed to novel compounds of the general Formula (XIII) and pharmaceutically acceptable salts thereof:

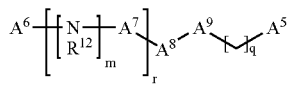

wherein $A^7$ is independently C=O, C=S, $SO_2$, CH—$OR^{13}$, C=$NR^{12}$, or $CH_2$—$CHOR^{13}$;

$A^8$ is independently $C(R^{14})_2$, O, S, or $NR^{12}$;

$A^9$ is independently C=O, C=S, $SO_2$, CH—$OR^{13}$, C=$NR^{12}$, or $CH_2$—$CHOR^{13}$;

m is 0, or 1 q is 0, or 1

$R^{12}$ is independently H, $CH_3$, $CH_2$—$CH_3$, $C_6H_5$, $OCH_3$, $OCH_2$—$CH_3$, OH, or SH;

$R^{13}$ is independently H, $CH_3$, or $CH_2$—$CH_3$;

$R^{14}$ is independently H, alkyl, alkoxy, OH, or SH;

$A^5$ is an optionally substituted $C_3$-$C_{16}$-alkyl group by one or more substituents $R^3$ or an optionally substituted 5 or 6-membered heteroaryl group, which contains at least one heteroatom like O, N, S, $NR^4$, SO, $SO_2$, Se; which can optionally be substituted by one or more substituents $R^3$;

$A^6$ is a substituted aryl group, which contains at least one heteroatom like O, N, S, $NR^4$, SO, $SO_2$, Se; which can optionally be substituted by one or more substituents $R^8$, $R^{8'}$, or $R^9$, or an optionally substituted heteroaryl group, which contains at least one heteroatom like O, N, S, $NR^4$, SO, $SO_2$, Se; which can optionally be substituted by one or more substituents $R^8$, $R^{8'}$, or $R^9$, or a heterocyclic group, which contains at least one double bond, and which may contain a heteroatom like O, N, S, $NR^4$, SO, $SO_2$, Se; which can optionally be substituted by one or more substituents $R^8$, $R^{8'}$, or $R^9$, or one of the groups mentioned below:

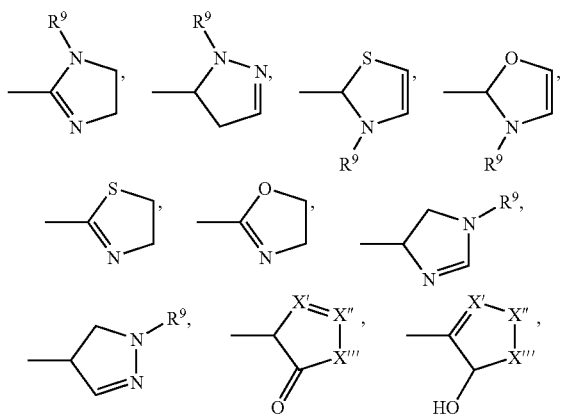

-continued

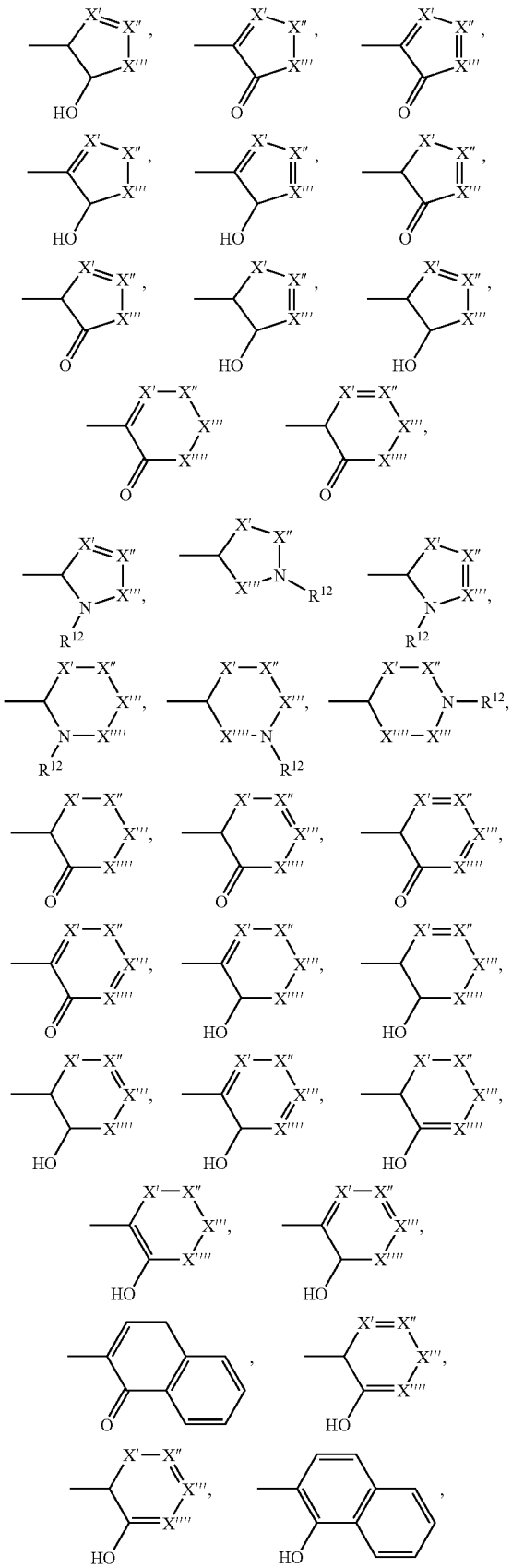

-continued

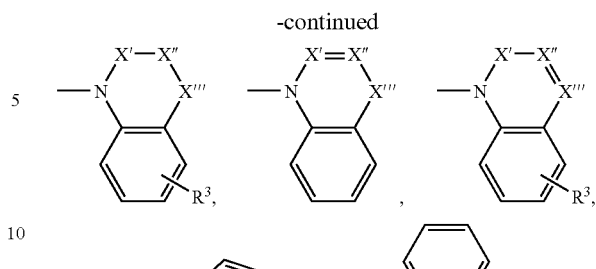

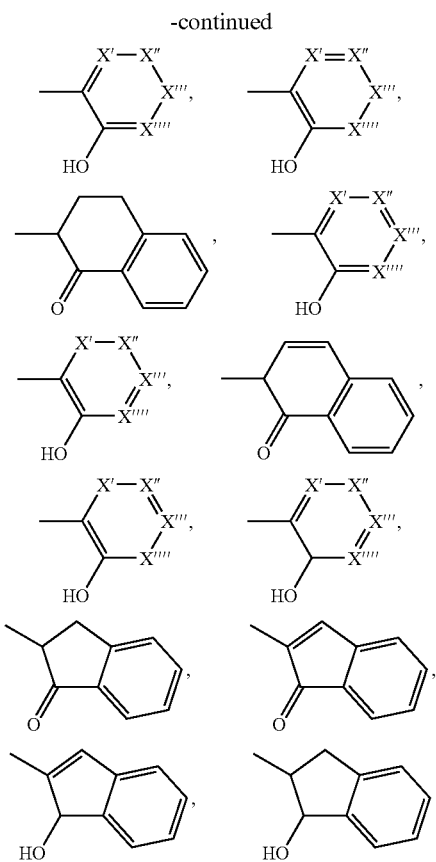

or one of the groups mentioned below: wherein m=0,

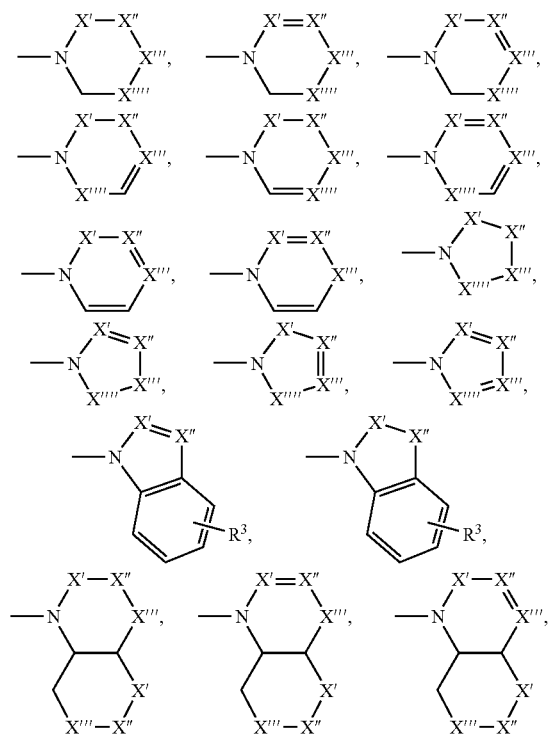

or one of the groups mentioned below; wherein m and r=0,

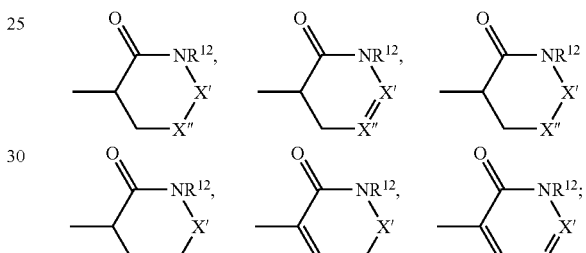

wherein X', X", X''', X'''' is independently S, O, N, NR⁴, CO, SO, SO₂, CR³', or CR³'R⁴';

R⁸, R⁸', R⁹ is independently H, methyl, ethyl, t-butyl, CN, halogen, haloalkoxy, haloalkyl, OH, oxy, NR⁴R⁵, COOR⁴;

R³' is independently H, OR⁴, SR⁴, hydroxyalkyl, hydroxyalkylamino, cycloalkyl, halogen, haloalkyl, haloalkyloxy, NO₂, CN, SO₂NR⁴R⁵, CONR⁴R⁵, COR⁴, CO₂R⁴, SO₂R⁴, SO₃R⁴, NR⁴R⁵, alkyl, aryl, or heteroaryl;

R⁴' is H, alkyl, cycloalkyl, aryl or heteroaryl;

R³ is independently H, OR⁴, SR⁴, hydroxyalkyl, hydroxyalkylamino, cycloalkyl, halogen, haloalkyl, haloalkyloxy, NO₂, CN, SO₂NR⁴R⁵, CONR⁴R⁵, COR⁴, CO₂R⁴, SO₂R⁴, SO₃R⁴, NR⁴R⁵, alkyl aryl or heteroaryl;

R⁴ is H, alkyl, cycloalkyl, aryl or heteroaryl;

R⁵ is H, O-alkyl, O-aryl, alkyl, heteroaryl or aryl;

said heteroaryl group of A⁵ or A⁶ may be selected from the group comprising:

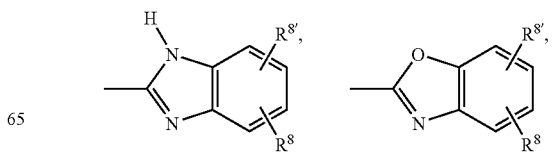

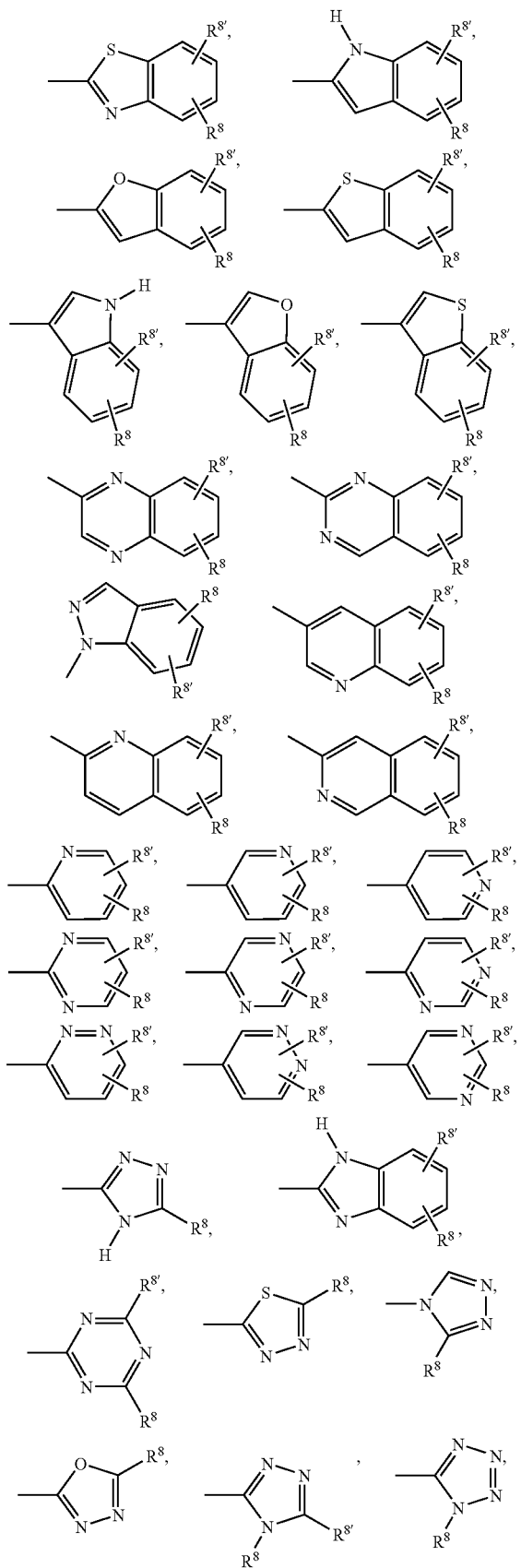
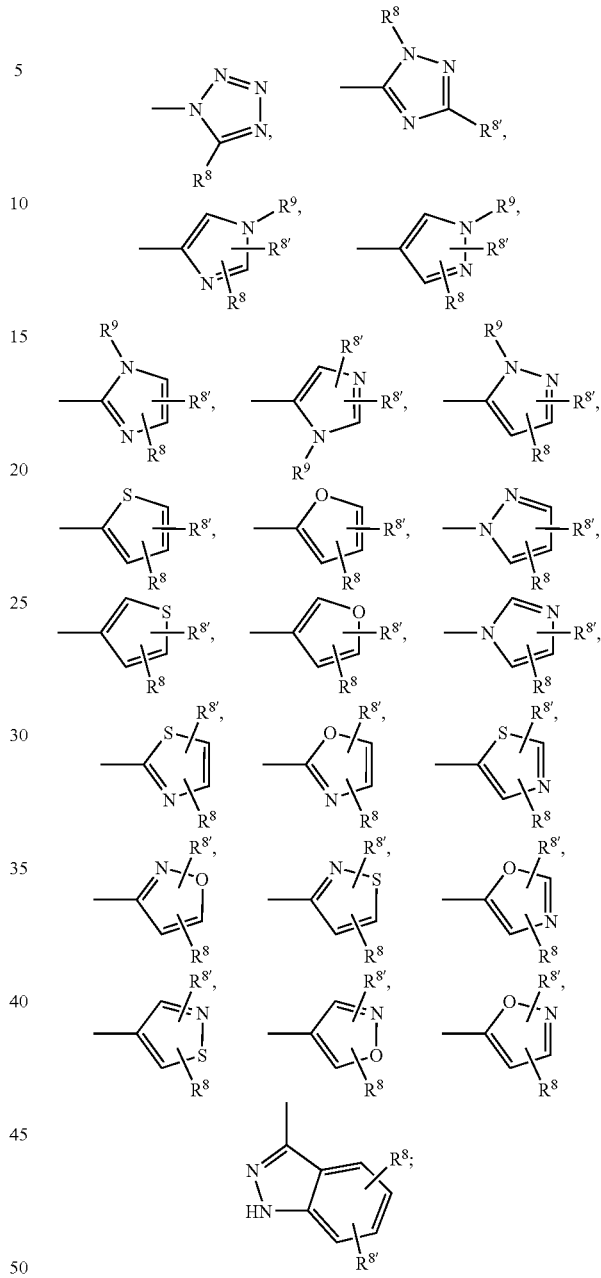

said $C_3$-$C_{16}$-alkyl residue may be selected from the group comprising —$C_3H_7$, —$CH(CH_3)_2$, —$C_4H_9$, —$CH_2$—CH$(CH_3)_2$, —$CH(CH_3)$—$C_2H_5$, —$CH_2$—$CH(CH_3)$—$CH_3$, —$C(CH_3)_3$, —$C_5H_{11}$, —$C_2H_4$—$CH(CH_3)_2$, —$CH(CH_3)$—$C_3H_7$, —$CH_2$—$CH(CH_3)$—$C_2H_5$, —$CH(CH_3)$—$CH(CH_3)_2$, —$C(CH_3)_2$—$C_2H_5$, —$CH_2$—$C(CH_3)_3$, —$C_6H_{13}$, —$C_3H_6$—$CH(CH_3)_2$, —$C_2H_4$—$CH(CH_3)$—$C_2H_5$, —$CH(CH_3)$—$C_4H_9$, —$CH_2$—$CH(CH_3)$—$C_3H_7$, —$CH(CH_3)$—$CH_2$—$CH(CH_3)_2$, —$CH(CH_3)$—$CH(CH_3)$—$C_2H_5$, —$CH_2$—$CH(CH_3)$—$CH(CH_3)_2$, —$CH_2$—$C(CH_3)_2$—$C_2H_5$, —$C(CH_3)_2$—$C_3H_7$, —$C(CH_3)_2$—$CH(CH_3)_2$, —$C_2H_4$—$C(CH_3)_3$, —$CH(CH_3)$—$C(CH_3)_3$, —$C_7H_{15}$, —$C_3H_6$—$C(CH_3)_3$, —$C_4H_8$—$CH(CH_3)_2$, —$C_3H_6$—$CH(CH_3)$—$C_2H_5$, —$C_2H_4$—$C(CH_3)_2$—$C_2H_5$, —$C_2H_4$—$CH(CH_3)$—$C_3H_7$, —CH$_2$—C(CH$_3$)$_2$—C$_3$H$_7$, —CH$_2$—CH(CH$_3$)—C$_4$H$_9$, —CH(CH$_3$)—C$_5$H$_{11}$, —C$_8$H$_{17}$, —C$_4$H$_8$—C(CH$_3$)$_3$, —C$_5$H$_{10}$—CH(CH$_3$)$_2$, —C$_4$H$_8$—CH(CH$_3$)—C$_2$H$_5$, —C$_3$H$_6$—C(CH$_3$)$_2$—C$_2$H$_5$, —C$_3$H$_6$—CH(CH$_3$)—C$_3$H$_7$, —C$_2$H$_4$—C(CH$_3$)$_2$—C$_3$H$_7$, —C$_2$H$_4$—CH(CH$_3$)—C$_4$H$_9$, —CH$_2$—C(CH$_3$)$_2$—C$_4$H$_9$, —CH$_2$—CH(CH$_3$)—C$_5$H$_{11}$, —C(CH$_3$)$_2$—C$_5$H$_{11}$, —CH(CH$_3$)—C$_6$H$_{13}$, —C$_9$H$_{19}$, —C$_5$H$_{10}$—C(CH$_3$)$_3$, —C$_6$H$_{12}$—CH(CH$_3$)$_2$, —C$_5$H$_{10}$—CH(CH$_3$)—C$_2$H$_5$, —C$_4$H$_8$—C(CH$_3$)$_2$—C$_2$H$_5$, —C$_4$H$_8$—CH(CH$_3$)—C$_3$H$_7$, —C$_3$H$_6$—C(CH$_3$)$_2$—C$_3$H$_7$, —C$_3$H$_6$—CH(CH$_3$)—C$_4$H$_9$, —C$_2$H$_4$—C(CH$_3$)$_2$—C$_4$H$_9$, —C$_2$H$_4$—CH(CH$_3$)—C$_5$H$_{11}$, —CH$_2$—C(CH$_3$)$_2$—C$_5$H$_{11}$, —CH$_2$CH(CH$_3$)—C$_6$H$_{13}$, —C(CH$_3$)$_2$—C$_6$H$_{13}$, —CH(CH$_3$)—C$_7$H$_{15}$, —C$_{10}$H$_{21}$, —C$_6$H$_{12}$—C(CH$_3$)$_3$, —C$_7$H$_{14}$—CH(CH$_3$)$_2$, —C$_6$H$_{12}$—CH(CH$_3$)—C$_2$H$_5$, —C$_5$H$_{10}$—C(CH$_3$)$_2$—C$_2$H$_5$, —C$_5$H$_{10}$—CH(CH$_3$)—C$_3$H$_7$, —C$_4$H$_8$—C(CH$_3$)$_2$—C$_3$H$_7$, —C$_4$H$_8$—CH(CH$_3$)—C$_4$H$_9$, —C$_3$H$_6$—C(CH$_3$)$_2$—C$_4$H$_9$, —C$_3$H$_6$—CH(CH$_3$)—C$_5$H$_{11}$, —C$_2$H$_4$—C(CH$_3$)$_2$—C$_5$H$_{11}$, —C$_2$H$_4$—CH(CH$_3$)—C$_6$H$_{13}$, —CH$_2$—C(CH$_3$)$_2$—C$_6$H$_{13}$, —CH$_2$—CH(CH$_3$)—C$_7$H$_{15}$, —C(CH$_3$)$_2$—C$_7$H$_{15}$, —CH(CH$_3$)—C$_8$H$_{17}$, —C$_{11}$H$_{23}$, —C$_7$H$_{14}$—C(CH$_3$)$_3$, —C$_8$H$_{16}$—CH(CH$_3$)$_2$, —C$_7$H$_{14}$—CH(CH$_3$)—C$_2$H$_5$, —C$_6$H$_{12}$—C(CH$_3$)$_2$—C$_2$H$_5$, —C$_6$H$_{12}$—CH(CH$_3$)—C$_3$H$_7$, —C$_5$H$_{10}$—C(CH$_3$)$_2$—C$_3$H$_7$, —C$_5$H$_{10}$—CH(CH$_3$)—C$_4$H$_9$, —C$_4$H$_8$—C(CH$_3$)$_2$—C$_4$H$_9$, —C$_4$H$_8$—CH(CH$_3$)—C$_5$H$_{11}$, —C$_3$H$_6$—C(CH$_3$)$_2$—C$_5$H$_{11}$, —C$_3$H$_6$—CH(CH$_3$)—C$_6$H$_{13}$, —C$_2$H$_4$—C(CH$_3$)$_2$—C$_6$H$_{13}$, —C$_2$H$_4$—CH(CH$_3$)—C$_7$H$_{15}$, —CH$_2$—C(CH$_3$)$_2$—C$_7$H$_{15}$, —CH$_2$—CH(CH$_3$)—C$_8$H$_{17}$, —C(CH$_3$)$_2$—C$_8$H$_{17}$, —CH(CH$_3$)—C$_9$H$_{19}$, —C$_{12}$H$_{25}$, —C$_8$H$_{16}$—C(CH$_3$)$_3$, —C$_9$H$_{18}$—CH(CH$_3$)$_2$, —C$_8$H$_{16}$—CH(CH$_3$)—C$_2$H$_5$, —C$_7$H$_{14}$—C(CH$_3$)$_2$—C$_2$H$_5$, —C$_7$H$_{14}$—CH(CH$_3$)—C$_3$H$_7$, —C$_6$H$_{12}$—C(CH$_3$)$_2$—C$_3$H$_7$, —C$_6$H$_{12}$—CH(CH$_3$)—C$_4$H$_9$, —C$_5$H$_{10}$—C(CH$_3$)$_2$—C$_4$H$_9$, —C$_5$H$_{10}$—CH(CH$_3$)—C$_5$H$_{11}$, —C$_4$H$_8$—C(CH$_3$)$_2$—C$_5$H$_{11}$, —C$_4$H$_8$—CH(CH$_3$)—C$_6$H$_{13}$, —C$_3$H$_6$—C(CH$_3$)$_2$—C$_6$H$_{13}$, —C$_3$H$_6$—CH(CH$_3$)—C$_7$H$_{15}$, C$_2$H$_4$—C(CH$_3$)$_2$—C$_7$H$_{15}$, —C$_2$H$_4$—CH(CH$_3$)—C$_8$H$_{17}$, CH$_2$—C(CH$_3$)$_2$—C$_8$H$_{17}$, —CH$_2$—CH(CH$_3$)—C$_9$H$_{19}$, —C(CH$_3$)$_2$—C$_9$H$_{19}$, —CH(CH$_3$)—C$_{10}$H$_{21}$;

an alkyl group, if not stated otherwise, denotes a linear or branched C$_1$-C$_6$-alkyl, preferably a linear or branched chain of one to five carbon atoms, a linear or branched C$_1$-C$_6$-alkenyl or a linear or branched C$_1$-C$_6$-alkinyl group, which can optionally be substituted by one or more substituents R$^3$, preferably by halogen;

the C$_1$-C$_6$-alkyl, C$_1$-C$_6$-alkenyl and C$_1$-C$_6$-alkinyl residue may be selected from the group comprising —CH$_3$, —C$_2$H$_5$, —CH=CH$_2$, —C≡CH, —C$_3$H$_7$, —CH(CH$_3$)$_2$, —CH$_2$—CH=CH$_2$, —C(CH$_3$)=CH$_2$, —CH=CH—CH$_3$, —C≡C—CH$_3$, —CH$_2$—C≡CH, —C$_4$H$_9$, —CH$_2$CH(CH$_3$)$_2$, —CH(CH$_3$)—C$_2$H$_5$, —C(CH$_3$)$_3$, —C$_5$H$_{11}$, —C$_6$H$_{13}$, —C(R$^3$)$_3$, —CR$^3$(R$^{3'}$)$_2$, —CR$^3$(R$^{3'}$)R$^{3''}$, —C$_2$(R$^3$)$_5$, —CH$_2$—C(R$^3$)$_3$, —CH$_2$—CR$^3$(R$^{3'}$)$_2$, —CH$_2$—CR$^3$(R$^{3'}$)R$^{3''}$, —C$_3$(R$^3$)$_7$, —C$_2$H$_4$—C(R$^3$)$_3$, —C$_2$H$_4$—CH=CH$_2$, —CH=CH—C$_2$H$_5$, —CH=C(CH$_3$)$_2$, —CH$_2$—CH=CH—CH$_3$, —CH=CH—CH=CH$_2$, —C$_2$H$_4$—C≡CH, —C≡C—C$_2$H$_5$, —CH$_2$—C≡C—CH$_3$, —C≡C—CH=CH$_2$, —CH=CH—C≡CH, —C≡C—C≡CH, —C$_2$H$_4$—CH(CH$_3$)$_2$, —CH(CH$_3$)—C$_3$H$_7$, —CH$_2$—CH(CH$_3$)—C$_2$H$_5$, —CH(CH$_3$)—CH(CH$_3$)$_2$, —C(CH$_3$)$_2$—C$_2$H$_5$, —CH$_2$—C(CH$_3$)$_3$, —C$_3$H$_6$—CH=CH$_2$, —CH=CH—C$_3$H$_7$, —C$_2$H$_4$—CH=CH—CH$_3$, —CH$_2$—CH=CH—C$_2$H$_5$, —CH$_2$—CH=CH—CH$_3$, —CH=CH—CH=CH—CH$_3$, —CH=CH—CH$_2$—CH=CH$_2$, —C(CH$_3$)=CH—CH=CH$_2$, —CH=C(CH$_3$)—CH=CH$_2$, —CH=CH—C(CH$_3$)=CH$_2$, —CH$_2$— CH=C(CH$_3$)$_2$, —C(CH$_3$)=CH—C$_3$H$_7$, —C$_3$H$_6$—C≡CH, —C≡C—C$_3$H$_7$, —C$_2$H$_4$—C≡C—CH$_3$, —CH$_2$—C≡C—C$_2$H$_5$, —CH$_2$—C≡C—CH=CH$_2$, —CH$_2$—CH=CH—C≡CH, —CH$_2$—C≡C—C≡CH, —C≡C—CH=CH—CH$_3$, —CH=CH—C≡C—CH$_3$, —C≡C—C≡C—CH$_3$, —C≡C—CH$_2$—CH=CH$_2$, —CH=CH—CH$_2$—C≡CH, —C≡C—CH$_2$—C≡CH, —C(CH$_3$)=CH—CH=CH$_2$, —CH=C(CH$_3$)—CH=CH$_2$, —CH=CH—C(CH$_3$) =CH$_2$, —C(CH$_3$)=CH—C≡CH, —CH=C(CH$_3$)—C≡CH, —C≡C—C(CH$_3$)=CH$_2$, —C$_3$H$_6$—CH(CH$_3$)$_2$, —C$_2$H$_4$—CH(CH$_3$)—C$_2$H$_5$, —CH(CH$_3$)—C$_4$H$_9$, —CH$_2$—CH(CH$_3$)—C$_3$H$_7$, —CH(CH$_3$)—CH$_2$—CH(CH$_3$)$_2$, —CH(CH$_3$)—CH(CH$_3$)—C$_2$H$_5$, —CH$_2$—CH(CH$_3$)—CH(CH$_3$)$_2$, —CH$_2$—C(CH$_3$)$_2$—C$_2$H$_5$, —C(CH$_3$)$_2$—C$_3$H$_7$, —C(CH$_3$)$_2$—CH(CH$_3$)$_2$, —C$_2$H$_4$—C(CH$_3$)$_3$, —CH(CH$_3$)—C(CH$_3$)$_3$, —C$_4$H$_8$—CH=CH$_2$, —CH=CH—C$_4$H$_9$, —C$_3$H$_6$—CH=CH—CH$_3$, —CH$_2$—CH=CH—C$_3$H$_7$, —C$_2$H$_4$—CH=CH—C$_2$H$_5$, —CH$_2$—C(CH$_3$)=C (CH$_3$)$_2$, —C$_2$H$_4$—CH=C(CH$_3$)$_2$, —C$_4$H$_8$—C≡CH, —C≡C C$_4$H$_9$, —C$_3$H$_6$—C≡C—CH$_3$, —CH$_2$—C≡C—C$_3$H$_7$, —C$_2$H$_4$—C≡C—C$_2$H$_5$; R$^3$, R$^{3'}$ or R$^{3''}$ being as defined above;

a cycloalkyl group denotes a non-aromatic ring system containing three to eight carbon atoms, preferably four to eight carbon atoms, wherein one or more of the carbon atoms in the ring can be substituted by a group X, X being as defined above; the C$_3$-C$_8$-cycloalkyl residue may be selected from the group comprising -cyclo-C$_3$H$_5$, -cyclo-C$_4$H$_7$, -cyclo-C$_5$H$_9$, -cyclo-C$_6$H$_{11}$, -cyclo-C$_7$H$_{13}$, cyclo-C$_8$H$_{15}$;

an alkoxy group denotes an O-alkyl group, the alkyl group being as defined above; the alkoxy group is preferably a methoxy, ethoxy, isopropoxy, t-butoxy or pentoxy group, an haloalkyl group denotes an alkyl group which is substituted by one to five halogen atoms, the alkyl group being as defined above; the haloalkyl group is preferably a —C(R$^{10}$)$_3$, —CR$^{10}$(R$^{10'}$)$_2$, —CR$^{10}$(R$^{10'}$)R$^{10''}$, —C$_2$(R$^{10}$)$_5$, —CH$_2$—C(R$^{10}$)$_3$, —CH$_2$—CR$^{10}$(R$^{10'}$)$_2$, —CH$_2$—CR$^{10}$(R$^{10'}$)R$^{10''}$, —C$_3$(R$^{10}$)$_7$ or —C$_2$H$_4$—C(R$^{10}$)$_3$, wherein R$^{10}$, R$^{10'}$, R$^{10''}$ represent F, Cl, Br or I, preferably F;

a hydroxyalkyl group denotes an HO-alkyl group, the alkyl group being as defined above;

an haloalkyloxy group denotes an alkoxy group which is substituted by one to five halogen atoms, the alkyl group being as defined above; the haloalkyloxy group is preferably a —OC(R$^{10}$)$_3$, —OCR$^{10}$(R$^{10'}$)$_2$, —OCR$^{10}$(R$^{10'}$)R$^{10''}$, —OC$_2$(R$^{10}$)$_5$, —OCH$_2$—C(R$^{10}$)$_3$, —OCH$_2$—CR$^{10}$(R$^{10'}$)$_2$, —OCH$_2$—CR$^{10}$(R$^{10'}$)R$^{10''}$, —OC$_3$(R$^{10}$)$_7$ or —OC$_2$H$_4$—C(R$^{10}$)$_3$, wherein R$^{10}$, R$^{10'}$, R$^{10''}$ represent F, Cl, Br or I, preferably F;

a hydroxyalkylamino group denotes an (HO-alkyl)$_2$-N— group or HO-alkyl-NH— group, the alkyl group being as defined above;

a halogen group is chlorine, bromine, fluorine or iodine;

an aryl group preferably denotes an aromatic group having five to fifteen carbon atoms, which can optionally be substituted by one or more substituents R$^3$, where R$^3$ is as defined above; the aryl group is preferably a phenyl group, —CH$_2$—C$_6$H$_4$, —C$_2$H$_4$—C$_6$H$_4$, —CH=CH—C$_6$H$_4$, —C≡C—C$_6$H$_4$, -o-C$_6$H$_4$—R$^3$, -m-C$_6$H$_4$—R$^3$, -p-C$_6$H$_4$—R$^3$, -o-CH$_2$—C$_6$H$_4$—R$^3$, -m-CH$_2$—C$_6$H$_4$—R$^3$, -p-CH$_2$—C$_6$H$_4$—R$^3$;

a heteroaryl group denotes a 5- or 6-membered heterocyclic group which contains at least one heteroatom like O, N, S. This heterocyclic group can be fused to another ring. For example, this group can be selected from an oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, 1,2,4-oxadiazol-3-yl, 1,2,4-oxadiazol-5-yl, 1,2,4-thiadiazol-3-yl, 1,2,4-thiadiazol-5-yl, 1,2,5-oxadiazol-3-yl, 1,2,5-oxadiazol-4-yl, 1,2,5-thiadiazol-3-yl, 1-imidazolyl, 2-imidazolyl, 1,2,5-thiadiazol-4-yl, 4-imidazolyl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-pyrazinyl, 1-pyrazolyl, 3-pyrazolyl, 4-pyrazolyl, indolyl, indolinyl, benzo-[b]-furanyl, benzo[b]thiophenyl, benzimidazolyl, benzothiazolyl, quinazolinyl, quinoxazolinyl, or preferably isoxazol-3-yl, isoxazol-4-yl, isoxazol-5-yl, quinolinyl, tetrahydroquinolinyl, isoquinolinyl, tetrahydroisoquinolinyl group. This heterocyclic group can optionally be substituted by one or more substituents $R^3$, where $R^3$ is as defined above.

The invention also provides a pharmaceutical composition comprising a compound of Formula (XIII) or of Formula (I) in free form or in the form of pharmaceutically acceptable salts and physiologically functional derivatives, together with a pharmaceutically acceptable diluent or carrier therefore.

The term "physiologically functional derivative" as used herein refers to compounds which are not pharmaceutically active themselves but which are transformed into their pharmaceutical active form in vivo, i.e. in the subject to which the compound is administered.

In another aspect, the present invention also provides a method for the treatment or prophylaxis of a condition where there is an advantage in inhibiting quorum sensing which comprises the administration of an effective amount of a compound of Formula (XIII) or of Formula (I) and physiologically acceptable salts or physiologically functional derivatives thereof. The term "quorum sensing" is intended to describe cell-density dependent gene regulation through a diffusible signal molecule (Fuqua et al., J. Bacteriol. 176:269-75, 1994).

The invention is also directed to the use of compounds of Formula (XIII) or of Formula (I) and of their pharmacologically tolerable salts or physiologically functional derivatives for the production of a medicament or medical device for the prevention and treatment of diseases, where quorum sensing inhibition is beneficial. Furthermore, the invention is also directed to the use of compounds of Formula (XIII) or of Formula (I) and of their pharmacologically tolerable salts or physiologically functional derivatives for the production of an antibacterial agent for the prevention and treatment of bacterial biofilms in industrial and environmental settings.

In addition, the present invention provides methods for preparing the desired compounds of Formula (XIII) or of Formula (I).

One possibility for preparing the compounds of Formula (XIII) ($A^7$, $A^9$=CO, $A^8$=$CH_2$) comprises the step of reacting a compound of Formula (XIV) with a compound of the Formula (XV). For example, this method is described in Synthesis 1992, 1213-1214.

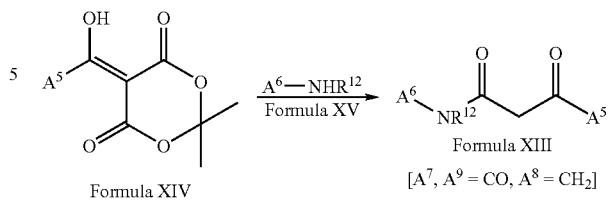

One possibility for preparing the compounds of Formula (XIII) ($A^7$, $A^9$=CO, $A^8$=$CH_2$, m=0) comprises the step of reacting a compound of Formula (XIV) with a compound of the Formula (XVI). For example, this method is described in Synthesis 1992, 1213-1214.

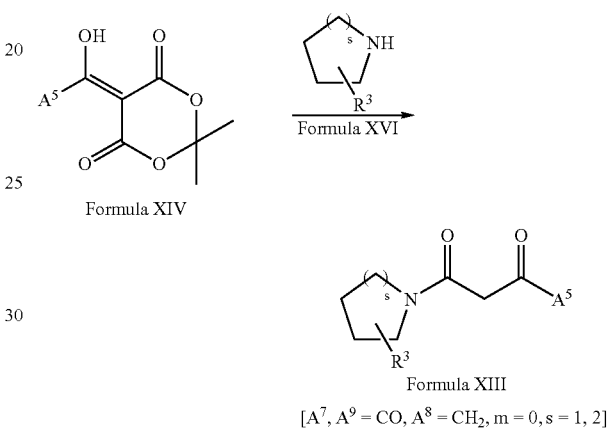

One method for preparation of compounds of Formula (XIV) comprises the step of reacting a carboxylic acid chloride with Meldrum's acid in presence of a base. For example, this reaction is described in Org. Synth., Coll. Vol. 7, 359-360 (Org. Synth. 1984, Ann. Vol. 63, 198-199), or J. Org. Chem. 1978, 43, 2087-2088, and Bull. Chem. Soc. Jpn. 1982, 55, 2186-2189.

Another possibility for preparing compounds of Formula (XIII) ($A^7$, $A^9$=CO, $A^8$=$CH_2$) comprises the reaction of a 3-oxo carboxylic acid chloride with a compound of Formula (XV). For example, this procedure is described in Chem. Pharm. Bull. 1980, 28, 2494-2502.

Another possibility for preparing compounds of Formula (XIII) ($A^7$, $A^9$=CO, $A^8$=$CH_2$) comprises the reaction of a 3-oxo carboxylic acid ester with a compound of Formula (XV). For example, this procedure is described in Gazz. Chim. Ital. 1936, 66, 723-731.

Another possibility for preparing the compounds of Formula (XIII) ($A^7$, $A^9$=CO, $A^8$=$CH_2$) comprises the reaction of a 3-oxo carboxylic acid with or without 3-oxo protection with a compound of Formula (XV) using a peptide coupling method. For example, is procedure is described in Tetrahedron Lett. 1996, 37, 1883-1884, and Chem. Biol. 2003, 10, 81-89.

Another possibility for preparing compounds of Formula (XIII) ($A^7$, $A^9$=CO, $A^8$=$CH_2$) comprises the reaction of a deprotonated methyl ketone with an isocyanate. For example, this method is described in J. Med. Chem. 1993, 36, 2943-2949, or J. Med. Chem. 1993, 36, 3386-3396.

Other methods for preparing compounds of Formula (XIII) are described in Chem. Pharm. Bull. 1984, 32, 3848-

3856, or *Tetrahedron Lett.* 2001, 5195-5197, and *J. Am. Chem. Soc.* 1995, 117, 12360-12361.

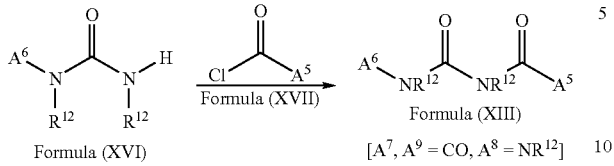

One possibility for preparing the compounds of Formula (XIII) ($A^7$, $A^9$=CO, $A^8$=$NR^{12}$) comprises the step of reacting a compound of Formula (XVI) with a compound of Formula (XVII). For example, this method is described in *Farmaco Ed. Sci.* 1982, 37, 335-342, or in *Monatsh. Chemie* 1981, 112, 871-874, or in *Monatsh. Chemie* 1982, 113, 101-110, or in *J. Am. Chem. Soc.* 2000, 122, 8155-8167, or in *Synth. Commun.* 1989, 19, 3543-3552.

Preferably, $R^3$ in Formula (XI) is independently H, halogen, methyl, 2-hydroxyethyl, $CF_3$, $OCF_3$, $CO_2R^4$ phenyl or alkyl.

$R^4$ in Formula (XIII) is independently H, alkyl, cycloalkyl, aryl or heteroaryl. Preferably $R^4$ is H.

$R^5$ in Formula (XIII) is independently H, O-alkyl, O-aryl, alkyl, heteroaryl or aryl.

Preferably $R^5$ is H.

A preferred compound of Formula (XIII) is a compound wherein $R^{14}$ is H or methyl more preferably H.

A preferred compound of Formula (XIII) is a compound wherein $R^{12}$ is H, phenyl or methyl more preferably H.

A preferred compound of Formula (XIII) is a compound wherein $A^8$ is $CH_2$.

A preferred compound of Formula (XIII) is a compound wherein $A^7$ and/or $A^9$ are CO.

A preferred compound of Formula (XIII) is a compound wherein $A^5$ is $C_6$-$C_{11}$-alkyl.

A preferred compound of Formula (XIII) is a compound wherein $A^6$ selected from the following group:

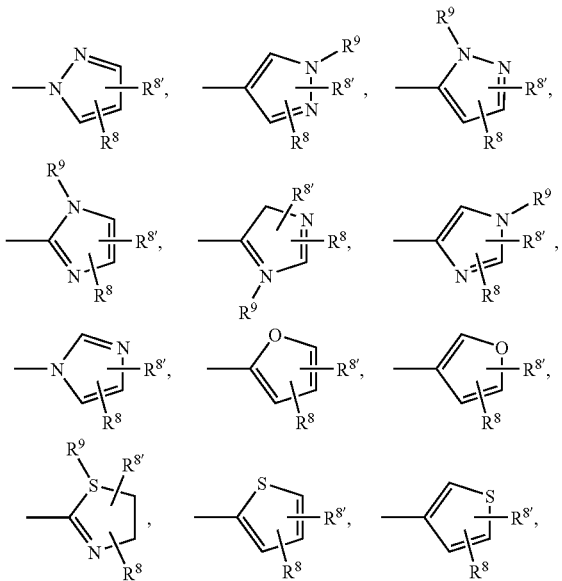

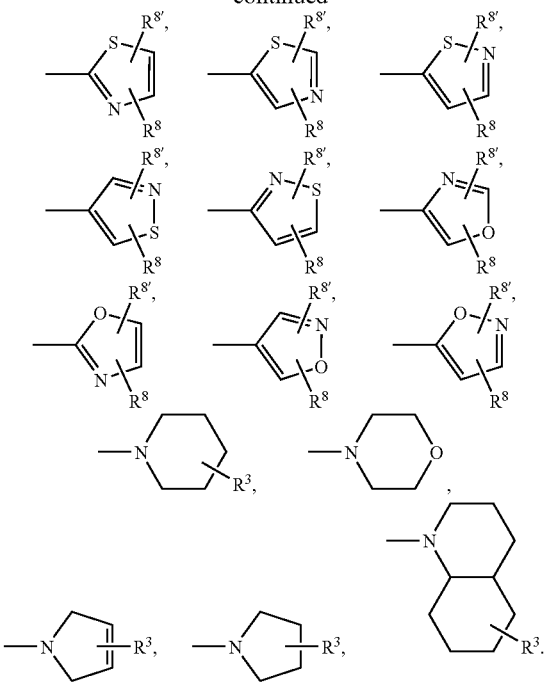

A preferred compound of Formula (XIII) is a compound wherein $A^6$ is 5-membered heteroaromatic ring system, m is 1, r is 1, q is 0 and $R^{12}$ is hydrogen.

A preferred compound of Formula (XIII) is a compound wherein $A^6$ is

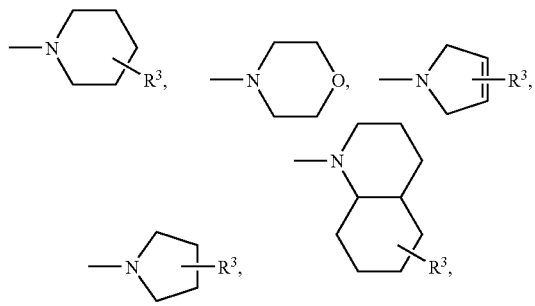

m is 0, r is 1, q is 0, and $R^3$ is methyl, 2-hydroxyethyl, or carboxyl.

A preferred compound of Formula (XIII) is a compound wherein $A^6$ is by $R^9$ substituted phenyl, m is 1, r is 1, q is 0 and $R^{12}$ is methyl or phenyl.

A preferred compound of Formula (XIII) is a compound wherein q is 0 and m, r are 1.

A preferred compound of Formula (XIII) is a compound wherein r is 1 and m, q are 0.

A preferred compound of Formula (XIII) is a compound wherein $R^{13}$ is H.

A preferred compound of Formula (XIII) is a compound wherein $R^8$, $R^{8'}$, or $R^9$ are H, methyl halogen, hydroxy, or carboxy.

Preferred compounds of the present invention and/or pharmaceutically acceptable salts thereof are selected from the group comprising:

3-Oxo-nonanoic acid (2H-pyrazol-3-yl)-amide; 3-Oxo-nonanoic acid (2-methyl-2H-pyrazol-3-yl)-amide; 3-Oxo-dodecanoic acid (2-methyl-2H-pyrazol-3-yl)-amide; 3-Oxo-nonanoic acid (2-ethyl-2H-pyrazol-3-yl)-amide; 3-Oxo-dodecanoic acid (2-ethyl-2H-pyrazol-3-yl)-amide; 3-Oxo-nonanoic acid (2,5 dimethyl-2H-pyrazol-3-yl)-amide; 3-Oxo-dodecanoic acid (2,5-dimethyl-2H-pyrazol-3-yl)-amide; 3-Oxo-nonanoic acid pyrazol-1-ylamide; 2-(3-Oxo-nonanoylamino)-thiophene-3-carboxylic acid methyl ester; 2-(3-Oxo-dodecanoylamino)-thiophene-3-carboxylic acid methyl ester; 4-Methyl-2-(3-oxo-nonanoylamino)-thiophene-3-carboxylic acid ethyl ester; 4-Methyl-2-(3-oxo-dodecanoylamino)-thiophene-3-carboxylic acid ethyl ester, 3-Oxo-nonanoic acid (3-methyl-isothiazol-5-yl)-amide; 3-Oxo-dodecanoic acid (3-methyl-isothiazol-5-yl)-amide; 3-Oxo-nonanoic acid thiazol-2-ylamide; 3-Oxo-dodecanoic acid thiazol-2-ylamide; 3-Oxo-nonanoic acid (5-acetyl-2-methylsulfanyl-thiazol-4-yl)-amide; 3-Oxo-nonanoic acid isoxazol-3-ylamide; 3-Oxo-dodecanoic acid isoxazol-3-ylamide; 3-Oxo-nonanoic acid (3-methyl-isoxazol-5-yl)-amide; 3-Oxo-dodecanoic acid (3-methyl-isoxazol-5-yl)-amide; 3-Oxo-nonanoic acid (4-methyl-oxazol-2-yl)-amide; 3-Oxo-nonanoic acid (4cyano-2-methyl-oxazol-5-yl)-amide; 3-Oxo-nonanoic acid (3-cyano-4,5-dimethyl-furan-2yl)-amide; 3-Oxo-dodecanoic acid (3-cyano-4,5-dimethyl-furan-2-yl)-amide; 5-(3 Oxo-nonanoylamino)-furan-2-carboxylic acid methyl ester; 3-Oxo-nonanoic acid (1H-pyrazol-3-yl)-amide; 3-Oxo-tetradecanoic acid (2,5-dimethyl-2H-pyrazol-3-yl)-amide; 2-(3-Oxo-tetradecanoylamino)-thiophene-3-carboxylic acid methyl ester, 4-Methyl-2-(3-oxo-tetradecanoylamino)-thiophene-3-carboxylic acid ethyl ester; 3-Oxo-nonanoic acid isoxazol-5-ylamide; 3-Oxo-dodecanoic acid isoxazol-5-ylamide; 3-Oxo-tetradecanoic acid isoxazol-5-ylamide; 3-Oxo-tetradecanoic acid (3-methyl-isoxazol-5-yl)-amide; 3-Oxo-dodecanoic acid (4-methyl-oxazol-2-yl)-amide; 3-Oxo-tetradecanoic acid (4-methyl-oxazol-2-yl)-amide; 5-(3-Oxo-dodecanoylamino)-furan-2-carboxylic acid methyl ester; 5-(3-Oxo-tetradecanoylamino)-furan-2-carboxylic acid methyl ester; 1-Piperidin-1-yl-dodecane-1;3-dione; 1-(2-Methyl-piperidin-1-yl)-dodecane-1,3-dione; 1-(3-Methyl-piperidin-1-yl)-dodecane-1,3-dione; 1-(2-Hydroxymethyl-piperidin-1-yl)-dodecane-1,3-dione; 1-(3-Oxo-dodecanoyl)-piperidine-2-carboxylic acid; 1-(3-Oxo-dodecanoyl)-piperidine-2-carboxylic acid ethyl ester; 3,3,3-Trifluoro-2-[1-3-oxo-dodecanoyl)-piperidin-2-ylmethyl]-propionic acid; 1-(3-Oxo-dodecanoyl)-piperidine-3-carboxylic acid diethylamide; 1-(Octahydro-quinolin-1-yl)-dodecane-1,3-dione; 5-Cyclopentyl-1-(2-methyl-piperidin-1-yl)-pentane-1,3-dione; 1-(4-Methyl-piperazin-1-yl)-dodecane-1,3-dione; 1-Morpholin-4-yl-dodecane-1,3-dione; 1-(2-Methyl-pyrrolidin-1-yl)-dodecane-1,3-dione; 1-(2-Methyl-5-oxo-pyrrolidin-1-yl)-dodecane-1,3-dione; 1-(2-Methoxymethyl-pyrrolidin-1-yl)-dodecane-1,3-dione; 1-(2-Hydroxymethyl-pyrrolidin-1-yl)-dodecane-1,3-dione; 1-(3-Oxo-dodecanoyl)-pyrrolidine-2-carboxylic acid; 5-Oxo-1-(3-oxo-dodecanoyl)-pyrrolidine-2-carboxylic acid; 1-(3-Oxo-dodecanoyl)-pyrrolidine-2-carboxylic acid amide; 1-(3-Oxo-nonanoyl)-pyrrolidine-2-carboxylic acid methyl ester; 1-(3-Oxo-dodecanoyl)-pyrrolidine-2-carboxylic acid methyl ester, 1-(3-Dimethylamino-pyrrolidin-1-yl)-nonane-1,3-dione; 1-(3-Dimethylamino-pyrrolidin-1-yl)-dodecane-1,3-dione; 1-Carbazol-9-yl-dodecane-1,3-dione; 1-(2,3-Dihydro-indol-1-yl)-dodecane-1,3-dione; 1-Indol-1-yl-dodecane-1,3-dione; 1-(3-Oxo-dodecanoyl)-2,3-dihydro-1H-indole-2-carboxylic acid; 1-(2,5-Dihydro-pyrrol-1-yl)-dodecane-1,3-dione; 1-(2,5-Dimethyl-2,5-dihydro-pyrrol-1-yl)-dodecane-1,3-dione; 1-(1H-Pyrrol-2-yl)-dodecane-1,3-dione; 1-(1H-Pyrrol-2-yl)-nonane-1,3dione; 3-Oxo-dodecanoic acid diphenylamide; 3-Oxo-nonanoic acid methyl-phenyl-amide; 3-Oxo-dodecanoic acid methyl-phenyl-amide; 3-Oxo-nonanoic acid methyl-o-tolyl-amide; 3-Oxo-dodecanoic acid methyl-o-tolyl-amide; 3-Oxo-nonanoic acid (2-hydroxy-phenyl)-methyl-amide; 3-Oxo-dodecanoic acid (2-hydroxy-phenyl)-methyl-amide; 3-Oxo-nonanoic acid (2-methoxy-phenyl)-methyl-amide; 3-Oxo-dodecanoic acid (2-methoxy-phenyl)-methyl-amide; 2-[Methyl-(3-oxo-nonanoyl)-amino]-benzoic acid; 2-[Methyl-(3-oxo-dodecanoyl)-amino]-benzoic acid; 2-[Methyl-(3-oxo-dodecanoyl)-amino]-benzoic acid methyl ester; 2-[(5-Cyclopentyl-3-oxo-pentanoyl)-methyl-amino]-benzoic acid; 3-Oxo-nonanoic acid (4chloro-phenyl)-methyl-amide; 3-Oxo-dodecanoic acid (4-chloro-phenyl)-methyl-amide; 3-Oxo-tetradecanoic acid (4-chloro-phenyl)-methyl-amide; 3-oxo-nonanoic acid (4-fluoro-phenyl)-methyl-amide; 3-Oxo-dodecanoic acid (4-fluoro-phenyl)-methyl-amide; 3-Oxo-nonanoic acid methyl-(2-trifluoromethyl-phenyl)-amide; 3-Oxo-dodecanoic acid methyl-(2-trifluoromethyl-phenyl)-amide; 3-Oxo-nonanoic acid (4-bromo-phenyl)-methyl-amide; 3-Oxo-dodecanoic acid (4-bromo-phenyl)-methyl-amide; 3-Oxo-nonanoic acid methyl-(1-methyl-pyrrolidin-3-yl)-amide; 3-Oxo-dodecanoic acid methyl-(1-methyl-pyrrolidin-3-yl)-amide; 1-(2-Methyl-piperidin-1-yl)-dodecan-1-one; 1-Dodecanoyl-piperidine-2-carboxylic acid ethyl ester, 1-(2-Hydroxymethyl-pyrrolidin-1-yl)-dodecan-1-one; 3-Oxo-tetradecanoic acid pyrazol-1-ylamide; 3-Oxo-dodecanoic acid pyrazol-1-ylamide; 2-(Dodecanoyl-methyl-amino)-benzoic acid methyl ester, 2-(Dodecanoyl-methyl-amino)-benzoic acid; Dodecanoic acid (4-fluoro-phenyl)-methyl-amide; Dodecanoic acid methyl-(2-trifluoromethyl-phenyl)-amide; Dodecanoic acid methyl-o-tolyl-amide; Dodecanoic acid (2-methoxy-phenyl)-methyl-amide; Dodecanoic acid (4-bromo-phenyl)-methyl-amide The compounds of the Formula (XIII) or of Formula (I) according to the invention can be also used in form of the corresponding salts with inorganic or organic acids or bases. Examples of such salts are, e.g., alkali metal salts, in particular sodium and potassium salts, hydrochloride or ammonium salts.

Examples of pharmaceutically acceptable salts comprise without limitation non-toxic inorganic or organic salts such as acetate derived from acetic acid, aconitate derived from aconitic acid, ascorbate derived from ascorbic acid, benzoate derived from benzoic acid, cinnamate derived from cinnamic acid, citrate derived from citric acid, embonate derived from embonic acid, enantate derived from heptanoic acid, formiate derived from formic acid, fumarate derived from fumaric acid, glutamate derived from glutamic acid, glycolate derived from glycolic acid, chloride derived from hydrochloric acid, bromide derived from hydrobromic acid, lactate derived from lactic acid, maleate derived from maleic acid, malonate derived from malonic acid, mandelate derived from mandelic acid, methanesulfonate derived from methanesulfonic acid, naphtaline-2-sulfonate derived from naphtaline-2-sulfonic acid, nitrate derived from nitric acid, perchlorate derived from perchloric acid, phosphate derived from phosphoric acid, phthalate derived from phthalic acid, salicylate derived from salicylic acid, sorbate derived from sorbic acid, stearate derived from stearic acid, succinate derived from succinic acid, sulphate derived from sulphuric acid, tartrate derived from tartaric acid, toluene-p-sulfate derived from p-toluene-sulfonic acid and others. Such salts can be produced by methods known to someone of skill in the art and described in the prior art.

Other salts like oxalate derived from oxalic acid, which is not considered as pharmaceutically acceptable can be appropriate as intermediates for the production of compounds of the Formula (XIII) or of Formula (I) or a pharmaceutically acceptable salt thereof or stereoisomer thereof.

In general, the compounds of the present invention can be used to inhibit quorum sensing signaling of bacteria employing HSLs as signal molecules for cell-cell communication. Preferably, the compounds can be applied to the bacteria listed in Table 1, and more preferably to the bacteria of Table 1 that are pathogens. In the following it is explained that the compounds of the present invention can be used as antibacterial agents in various applications.

In a preferred form, the compounds of Formula (XIII) or of Formula (I) are useful for the treatment of a variety of human, animal and plant diseases, where bacterial pathogens regulate the expression of virulence genes and other phenotypes, e.g. biofilm formation, through an HSL-based quorum sensing system. Furthermore, as the list of organisms (see Table 1) employing quorum sensing signaling for their virulence continues to increase, the compounds of the invention can be used also for organisms which will be added to the above listed in future.

In a first embodiment, the compounds are useful for the treatment of mammalian in particular human diseases caused by bacteria through the inhibition of the bacterial quorum sensing cascade rendering the pathogen avirulent. Such diseases include endocarditis, respiratory and pulmonary infections (preferably in immunocompromized and cystic fibrosis patients), bacteremia, central nervous system infections, ear infections including external otitis, eye infections, bone and joint infections, urinary tract infections, gastrointestinal infections and skin and soft tissue infections including wound infections, pyoderma and dermatitis which all can be triggered by *Pseudomonas aeruginosa*. Furthermore, the compounds can be used for the treatment of pulmonary infections caused by *Burkholderia cepacia* (preferably in immunocompromized and cystic fibrosis patients), gastroenteritis and wound infections caused by *Aeromonas hydrophila*, sepsis in tropical and subtropical areas caused by *Chromobacterium violaceum*, diarrhoea with blood and haemolytic uremic syndrome (HUS) caused by *Escherichia coli*, yersiniosis triggered by *Yersinia enterocolitica* and *Y. pseudotuberculosis*, and transfusion-related sepsis and fistulous pyoderma caused by *Serratia liquefaciens*.

In a second embodiment the compounds can be used in the treatment of immunological diseases, particularly autoimmune diseases such as psoriasis, rheumatoid arthritis, multiple sclerosis and type 1 (autoimmune) diabetes, of cardiovascuklar diseases such as cardiac tachyarrhythmias, ischaemic heart disease, congestive heart failure, of allergic diseases and of diseases including cancer, breast cancer, obesity, lipid metabolism disorders, immune disease, immune deficiency or immune disorders.

In a third embodiment, the compounds can be used to prevent and/or treat plant diseases, where inhibition of the HSL-mediated signaling system reduces or abolishes virulence of bacterial plant pathogens. Such diseases include crown gall tumors caused by *Agrobacterium tumefaciens*, soft rot caused by *Burkholderia cepacia, Erwinia carotovora* and *Erwinia chrysanthemi*, sweet corn and maize infections caused by *Pantoea stewartii* and wilt disease caused by *Ralstonia solanacearum*.

In a fourth embodiment, the compounds can be used for the prevention and/or treatment of animal diseases, preferably fish diseases such as septicemia caused by *Aeromonas hydrophila* and *Vibrio anguillarum*, furunculosis in salmonids caused by *Aeromonas salmonicida*, prawn infections caused by *Vibrio harveyi* and enteric redmouth disease caused by *Yersinia ruckeri*, but also for the prevention and/or treatment of insect diseases caused, for example, by *Xenorhabdus nematophilus*.

In general, the present invention provides a method for reducing the virulence of bacterial pathogens employing an HSL-based signaling system. In a preferred form, a method is provided to remove, diminish, detach or disperse a bacterial biofilm from a living or nonliving surface by treating the surface with a compound of Formula (XIII) or of Formula (I). This method is also useful to prevent biofilm formation on a living or nonliving surface by treating the surface with a compound of Formula (XIII) or of Formula (I) before bacterial colonization can initialize. The term "biofilm" refers to cell aggregations comprising either a single type of organism or a mixture of more then one organism, then also referred to as "mixed biofilms". It is clear to persons skilled in the art, that the compounds of the present invention can be applied in a wide variety of different fields such as environmental, industrial and medical applications in order to prevent and/or treat damages or diseases caused by bacteria.

In one aspect, the compounds of Formula (XIII) or of Formula (I) can be used for all kinds of surfaces in private and public areas, where it is beneficial to inhibit quorum sensing systems of Gram-negative bacteria in order to prevent and/or treat colonization and biofilm formation. The compounds here can be used in form of a solution, powder or as a coating. The compound is preferably applied to the surface as a solution of the compound, alone or together with other materials such as conventional surfactants, preferably sodium dodecyl sulfate, or detergents, biocides, fungicides, antibiotics, pH regulators, perfumes, dyes or colorants. In combination with a bacteriocidal agent, e.g., the compounds of Formula (XIII) or of Formula (I) inhibit virulence or biofilm formation whilst the bacteriocidal agent kills the pathogens.

In one embodiment, the compounds can be used as antibacterial agent for topical use in cleaning and treatment solutions such as disinfectants, detergents, household cleaner and washing powder formulations in the form of a spray or a dispensable liquid. In a preferred form, these solutions can be applied to windows, floors, clothes, kitchen and bathroom surfaces and other surfaces in the area of food preparation and personal hygiene. In addition, the compounds of Formula (XIII) or of Formula (I) can be used as antibacterial ingredients in personal hygiene articles, toiletries and cosmetics such as dentifrices, mouthwashes, soaps, shampoos, shower gels, ointments, creams, lotions, deodorants and disinfectants and storage solutions for contact lenses. In the case of contact lenses the compounds of Formula (XIII) or of Formula (I) can also be applied as coating or additive to the lens material.

In another embodiment, the compounds can be used to prevent or treat bacterial biofilms in industrial settings such as ship hulls, paper and metal manufacturing, oil recovery, food processing and other applications where process disturbances are referred to biofouling on surfaces. The compounds here can be used in form of a solution, paint or coating, for example as an ingredient in cooling lubricants. The compounds can also be applied to water processing plants or drinking water distribution systems where the colonized surface (preferably by *Pseudomonas aeruginosa*) is preferably the inside of an aqueous liquid system such as water pipes, water injection jets, heat exchangers and cooling towers. Until now biocides are the preferred tools to encounter these problems, but since biocides do not have a high specificity for bacteria, they are often toxic to humans as well. This can be circumvented by the application of the compounds of the present invention.

In a further embodiment, the present invention relates to a method of inhibiting and/or preventing medical device-associated bacterial infections. The invention provides articles coated and/or impregnated with a compound of Formula (XIII) or of Formula (I) in order to inhibit and/or prevent biofilm formation thereon. The articles are preferably surgical instruments, blood bag systems or medical devices; more preferably either permanently implanted devices such as artificial heart valve, prostethic joint, voice prosthesis, stent, shunt or not permanently implanted devices such as endotracheal or gastrointestinal tube, pacemaker, surgical pin or indwelling catheter.

In a more preferred form, the indwelling catheters are urinary catheters, vascular catheters, peritoneal dialysis catheter, central venous catheters and needleless connectors. The catheter materials can be polyvinylchloride, polyethylene, latex, teflon or similar polymeric materials, but preferably polyurethane and silicone or a mixture thereof. In order to reduce the risk of catheter-related bacterial infections, several catheters coated and/or impregnated with antiseptic or antimicrobial agents such as chlorhexidine/silver-sulfadiazine and minocycline/rifampin, respectively, have been developed. Furthermore, collection bags or layers sandwiched between an external surface sheath and a luminal silicone sheath have been constructed to overcome rapid loss of antimicrobial activity. Nevertheless, the emerging risk of bacterial resistance against traditional antibiotics limits the routine use of antibiotic-coated catheters.

The compounds of the present invention, however, offer the possibility to effectively reduce catheter-related bacterial infections with a low risk of resistance development due to a novel therapeutic strategy targeting highly sensitive signal transduction mechanisms in bacteria. The preferred form of application is the coating and/or impregnating of catheter materials on both the inner and outer catheter surfaces. More preferably, the compounds of Formula (XIII) or of Formula (I) can be included in a mixture of antibacterial agents released continously from a catheter-associated depot into the environment.

In a further embodiment, the compounds of the preset invention and their pharmacologically acceptable salts can be administered directly to animals, preferably to mammals, and in particular to humans as antibiotics per se, as mixture with one another or in the form of pharmaceutical preparations which allow enteral or parenteral use and which as active constituent contain an effective dose of at least one compound of the Formula (XIII) or of Formula (I) or a salt thereof, in addition to customary pharmaceutical excipients and additives. The compounds of Formula (XIII) or of Formula (I) can also be administered in form of their salts, which are obtainable by react the respective compounds with physiologically acceptable acids and bases.

The therapeutics can be administered orally, e.g., in the form of pills, tablets, coated tablets, sugar coated tablets, lozenges, hard and soft gelatin capsules, solutions, syrups, emulsions or suspensions or as aerosol mixtures. Administration, however, can also be carried out rectally, e.g., in the form of suppositories, or parenterally, e.g., in the form of injections or infusions, or percutaneously, e.g., in the form of ointments, creams or tinctures.

In addition to the active compounds of Formula (XIII) or of Formula (I) the pharmaceutical composition can contain further customary, usually inert carrier materials or excipients. Thus, the pharmaceutical preparations can also contain additives or adjuvants commonly used in galenic formulations, such as, e.g., fillers, extenders, disintegrants, binders, glidants, wetting agents, stabilizers, emulsifiers, preservatives, sweetening agents, colorants, flavorings or aromatizers, buffer substances, and furthermore solvents or solubilizers or agents for achieving a depot effect, as well as salts for modifying the osmotic pressure, coating agents or antioxidants. They can also contain two or more compounds of the Formula (XIII) or of Formula (I) or their pharmacologically acceptable salts and also other therapeutically active substances.

Thus, the compounds of the present invention can be used alone, in combination with other compounds of this invention or in combination with other active compounds, for example with active ingredients already known for the treatment of the afore mentioned diseases, whereby in the latter case a favorable additive effect is noticed. Suitable amounts to be administered to mammalian in particular humans range from 5 to 1000 mg.

To prepare the pharmaceutical preparations, pharmaceutically inert inorganic or organic excipients can be used. To prepare pill, tablets, coated tablets and hard gelatin capsules, e.g., lactose, corn starch or derivatives thereof, talc, stearic acid or its salts, etc. can be used. Excipients for soft gelatin capsules and suppositories are, e.g., fats, waxes, semi-solid and liquid polyols, natural or hardened oils etc. Suitable excipients for the production of solutions and syrups are, e.g., water, alcohol, sucrose, invert sugar, glucose, polyols etc. Suitable excipients for the production of injection solutions are, e.g., water, alcohol, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 0.1 to 100 mg/kg animal body weight preferably 1 to 50 mg/kg. Suitable dosage rates for larger mammals, e.g., humans, are of the order of from about 10 mg to 3 g/day, conveniently administered once, in divided doses 2 to 4 times a day, or in sustained release form.

In general, a daily dose of approximately 0.1 mg to 5000 mg, preferably 10 to 500 mg, per mammalian in particular human individual is appropriate in the case of the oral administration which is the preferred form of administration according to the invention. In the case of other administration forms too, the daily dose is in similar ranges. The compounds of Formula (XIII) or of Formula (I) can also be used in the form of a precursor (prodrug) or a suitably modified form, that releases the active compound in vivo.

In a further embodiment, the compounds of the present invention can be used as pharmacologically active components or ingredients of medical devices, instruments and articles with an effective dose of at least one compound of the Formula (XIII) or of Formula (I) or a salt thereof. The amount of the compounds used to cost for example medical device surfaces varies to some extent with the coating method and the application field. In general, however, the concentration range from about 0.01 mg per $cm^2$ to about 100 mg per $cm^2$. In a similar way the amount of the compounds has to be adjusted to the application mode if the compounds of the invention are used as components or ingredients in cleaning or treatment solutions. In general, effective dosages range from about 0.1 µM to about 1000 mM.

The following section shows examples for to synthesis of the compounds of the present invention and demonstrate their quorum sensing inhibiting effect.

EXAMPLES

1. Synthesis of Compounds of Formula (XIII) (β-Ketoamides)

The acyl Meldrum's acid (1.2 eq) was dissolved in anhydrous benzene (concentration approximately 0.4 mol/l), and the amine (1.0 eq) was added. In case of amine hydrochlorides, one equivalent of triethylamine or N,N-diisopropylethylamine was added. The mixture was refluxed until tlc showed complete conversion (typically, 4 to 6 h). The benzene solutions were directly chromatographed on silica gel in an appropriate solvent mixture (isohexane—ethyl acetate, dichloromethane—methanol, or dichloromethane—acetonitrile mixtures). Yields of the purified products typically were in the range from 30 to 75%.

In the following Table 2, the synthesis method employed in each case for the respective compound or whether the compound was obtained is indicated. Furthermore, the mass found by LC/(+)-ESI and LC/(−)-ESI mass spectrometry, the molecular mass, the NMR data (300.13 MHz, residual solvent peaks were used as internal standards (chloroform, δ 7.26; methanol, δ 3.31; dimethyl sulfoxide, δ 2.49; abbreviations; ψ=pseudo, br.=broad, s=singulet, d=doublet, t=triplet, q=quartet, quint.=quintet, sext.=sextet, $m_c$=multiplet centered, m=multiplet, $CH_{ar}$=aromatic H, J=$^1$H—$^1$H coupling constant) and the $IC_{50}$ range as a measure of anti-quorum sensing activity are indicated. The NMR data of the small signals due to enol-tautomers or possible rotamers of the 3-oxo-carboxylic acid amides are not listed.

TABLE 2

Structure and biofilm assay results of the tested compounds.

| # | Compound | HPLC/MS (ESI) | $^1$H—NMR (300 MHz) | Biofilm inhibition [%]* |
|---|---|---|---|---|
| 1 | (structure) | 238 [M + H]$^+$ 236 [M − H]$^−$ | δ (CDCl$_3$) = 0.86 (ψ-t, J≈7Hz, 1H, 9-H), 1.21-1.38 (m, 6H, 6-H, 7-H, 8-H), 1.59 (ψ-quint, J=7.3Hz, 2H, 5-H), 2.63 (t, J=7.4Hz, 2H, 4-H), 3.60 (s, 2H, 2-H), 6.61 (s, br., 1H, ring-H), 7.46 (s, br., 1H, ring-H), 10.61 (s, br., 1H, NH). | + |
| 2 | (structure) | 252 [M + H]$^+$ 250 [M − H]$^−$ | δ (CDCl$_3$) =0.89 (ψ-t, J≈7Hz, 1H, 9-H), 1.23-1.37 (m, 6H, 6-H, 7-H, 8-H), 1.63 (ψ-quint, J=7.3Hz, 2H, 5-H), 2.58 (t, J=7.3Hz, 2H, 4-H), 3.66 (s, 2H, 2-H), 3.87 (s, 2H, NCH$_3$), 6.44 (d, J=2.1Hz, 1H, ring-H), 7.47 (d, J=2.1Hz, 1H, ring-H), 9.85 (s, br., 1H, NH). | + |
| 3 | (structure) | 294 [M + H]$^+$ 292 [M − H]$^−$ | δ (CDCl$_3$) = 0.87 (ψ-t, J≈7Hz, 1H, 12-H), 1.19-1.37 (m, 12H, 6-H, 7-H, 8-H, 9-H, 10-H, 11-H), 1.61 (ψ-quint, J=7.3Hz, 2H, 5-H), 2.53 (t, J=7.3Hz, 2H, 4-H), 3.57 (s, 2H, 2-H), 3.75 (s, 2H, NCH$_3$), 6.30 (d, J=1.8Hz, 1H, ring-H), 7.38 (d, J=1.8Hz, 1H, ring-H), 9.55 (s, br., 1H, NH). | +++ |
| 4 | (structure) | 266 [M + H]$^+$ 264 [M − H]$^−$ | δ (CDCl$_3$) = 0.88 (ψ-t, J≈7Hz, 1H, 9-H), 1.23-1.36 (m, 6H, 6-H, 7-H, 8-H), 1.61 (ψ-quint, J=7.3Hz, 2H, 5-H), 2.22 (s, 3H, ring-CH$_3$), 2.57 (t, J=7.3Hz, 2H, 4-H), 3.60 (s, 2H, 2-H), 3.72 (s, 3H, NCH$_3$), 6.15 (s, 1H, ring-H), 9.58 (s, br., 1H, NH). | + |
| 5 | (structure) | 308 [M + H]$^+$ 306 [M − H]$^−$ | δ (CDCl$_3$) = 0.88 (ψ-t, J≈7Hz, 1H, 12-H), 1.21-1.36 (m, 12H, 6-H, 7-H, 8-H, 9-H, 10-H, 11-H), 1.63 (ψ-quint, J=7.3Hz, 2H, 5-H), 2.22 (s, 3H, ring-CH$_3$), 2.57 (t, J=7.3Hz, 2H, 4-H), 3.60 (s, 2H, 2-H), 3.72 (s, 3H, NCH$_3$), 6.14 (s, 1H, ring-H), 9.44 (s, br., 1H, NH). | + |
| 6 | (structure) | 236 [M + H]$^+$ 234 [M − H]$^−$ | — | + |
| 7 | (structure) | 238 [M + H]$^+$ 236 [M − H]$^−$ | δ (CDCl$_3$) = 0.88 (ψ-t, J≈7Hz, 1H, 9-H), 1.17-1.34 (m, 6H, 6-H, 7-H, 8-H), 1.59 (ψ-quint, J=7.3Hz, 2H, 5-H), 2.56 (t, J=7.3Hz, 2H, 4-H), 3.59 (s, 2H, 2-H), 6.31 (ψ-t, J=2.3Hz, 1H, ring-H), 7.44 (dd, J=2.3Hz, J=0.6Hz, 1H, ring-H), 7.49 (d, J≈2Hz, 1H, ring-H), 10.64 (s, br., 1H, NH). | + |

TABLE 2-continued

Structure and biofilm assay results of the tested compounds.

| # | Compound | HPLC/MS (ESI) | $^1$H—NMR (300 MHz) | Biofilm inhibition [%]* |
|---|---|---|---|---|
| 8 | | 280 [M + H]$^+$ 278 [M − H]$^-$ | — | + |
| 9 | | 308 [M + H]$^+$ 306 [M − H]$^-$ | — | + |
| 10 | | 312 [M + H]$^+$ 310 [M − H]$^-$ | δ (CDCl$_3$) = 0.88 (ψ-t, J≈7Hz, 1H, 9-H), 1.21-1.36 (m, 6H, 6-H, 7-H, 8-H), 1.65 (ψ-quint, J=7.3Hz, 2H, 5-H), 2.59 (t, J=7.3Hz, 2H, 4-H), 3.66 (s, 2H, 2-H), 3.94 (s, 3H, CO$_2$CH$_3$), 6.75 (dd, J=5.8Hz, J=0.8Hz, 1H, ring-H), 7.23 (d, J=5.8Hz, 1H, ring-H), 11.88 (s, br., 1H, NH). | + |
| 11 | | 354 [M + H]$^+$ 352 [M − H]$^-$ | δ (CDCl$_3$) 0.88 (ψ-t, J≈7Hz, 1H, 12-H), 1.21-1.36 (m, 12H, 6-H, 7-H, 8-H, 9-H, 10-H, 11-H), 1.65 (ψ-quint, J=7.3Hz, 2H, 5-H), 2.58 (t, J=7.3Hz, 2H, 4-H), 3.66 (s, 2H, 2-H), 3.93 (s, 3H, CO$_2$CH$_3$), 6.74 (dd, J=5.8Hz, J=0.8Hz, 1H, ring-H), 7.22 (d, J=5.8Hz, 1H, ring-H), 11.88 (s, br., 1H, NH). | + |
| 12 | | 382 [M + H]$^+$ 380 [M − H]$^-$ | — | + |
| 13 | | 340 [M + H]$^+$ 338 [M − H]$^-$ | δ (CDCl$_3$) 0.88 (ψ-t, J≈7Hz, 1H, 9-H), 1.24-1.35 (m, 6H, 6-H, 7-H, 8-H), 1.41 (t, J=7.1Hz, 3H, CO$_2$CH$_2$CH$_3$), 1.63 (ψ-quint, J=7.4Hz, 2H, 5-H), 2.38 (d, J=1.1Hz, 3H, ring-CH$_3$), 2.58 (t, J=7.3Hz, 2H, 4-H), 3.63 (s, 2H, 2-H), 4.42 (q, J=7.1Hz, 2H, CO$_2$CH$_2$CH$_3$), 6.39-6.41 (m, 1H, ring-H), 11.97(s, br., 1H, NH). | + |
| 14 | | 382 [M + H]$^+$ 380 [M − H]$^-$ | δ (CDCl$_3$) = 0.88 (ψ-t, J≈7Hz, 1H, 12-H), 1.21-1.36 (m, 12H, 6-H, 7-H, 8-H, 9-H, 10-H, 11-H), 1.41 (t, J=7.1Hz, 3H, CO$_2$CH$_2$CH$_3$), 1.63 (ψ-quint, J=7.4Hz, 2H, 5-H), 2.38 (d, J=1.1Hz, 3H, ring-CH$_3$), 2.58 (t, J=7.3Hz, 2H, 4-H), 3.63 (s, 2H, 2-H), 4.42 (q, J=7.1Hz, 2H, CO$_2$CH$_2$CH$_3$), 6.39-6.41(m, 1H, ring-H), 11.97 (s, br., 1H, NH). | + |
| 15 | | 410 [M + H]$^+$ 408 [M − H]$^-$ | | + |
| 16 | | 255 [M + H]$^+$ 253 [M − H]$^-$ | δ (CDCl$_3$) = 0.88 (ψ-t, J≈7Hz, 1H, 9-H), 1.24-1.37 (m, 6H, 6-H, 7-H, 8-H), 1.62 (ψ-quint, J=7.3Hz, 2H, 5-H), 2.59 (t, J=7.3Hz, 2H, 4-H), 3.71 (s, 2H, 2-H), 7.00 (d, J=3.7Hz, 1H, ring-H), 7.47 (d, J=3.7Hz, 1H, ring-H), [NH proton not visible]. | + |
| 17 | | 297 [M + H]$^+$ 295 [M − H]$^-$ | δ (CDCl$_3$) = 0.88 (ψ-t, J≈7Hz, 1H, 12-H), 1.21-1.37 (m, 12H, 6-H, 7-H, 8-H, 9-H, 10-H, 11-H), 1.62 (ψ-quint, J=7.3Hz, 2H, 5-H), 2.61 (t, J=7.3Hz, 2H, 4-H), 3.66 (s, 2H, 2-H), 7.00 (d, J=3.6Hz, 1H, ring-H), 7.49 (d, J=3.6Hz, 1H, ring-H), 11.54 (s, br., 1H, NH). | + |

TABLE 2-continued

Structure and biofilm assay results of the tested compounds.

| # | Compound | HPLC/MS (ESI) | ¹H—NMR (300 MHz) | Biofilm inhibition [%]* |
|---|---|---|---|---|
| 18 | (acetyl-methylthio-thiazole amide with hexyl β-ketoamide chain) | 343 [M + H]⁺ 341 [M − H]⁻ | δ (CDCl$_3$) = 0.85 (ψ-t, J≈7Hz, 1H, 9-H), 1.21-1.37 (m, 6H, 6-H, 7-H, 8-H), 1.59 (ψ-quint, J=7.3Hz, 2H, 5-H), 2.38 (s, 3H, SCH$_3$#), 2.56 (t, J=7.3Hz, 2H, 4-H), 2.68 (s, 3H, COCH$_3$#), 3.87 (s, br., 2H, 2-H), 10.88 (s, br., 1H, NH). | + |
| 19 | (isoxazole amide, hexyl β-ketoamide) | 239 [M + H]⁺ 237 [M − H]⁻ | — | ++ |
| 20 | (isoxazole amide, (CH$_2$)$_8$ β-ketoamide) | 281 [M + H]⁺ 279 [M − H]⁻ | — | + |
| 21 | (isoxazole amide, (CH$_2$)$_{10}$ β-ketoamide) | 309 [M + H]⁺ 307 [M − H]⁻ | — | + |
| 22 | (3-methylisoxazole amide, (CH$_2$)$_5$ β-ketoamide) | 253 [M + H]⁺ 251 [M − H]⁻ | δ (CDCl$_3$) = 0.89 (ψ-t, J≈7Hz, 1H, 9-H), 1.25-1.37 (m, 6H, 6-H, 7-H, 8-H), 1.63 (ψ-quint, J=7.3Hz, 2H, 5-H), 2.27 (s, 3H, ring-CH$_3$), 2.56 (t, J=7.3Hz, 2H, 4-H), 3.60 (s, 2H, 2-H), 6.20 (s, 1H, ring-H), 10.17 (s, br., 1H, NH). | + |
| 23 | (3-methylisoxazole amide, (CH$_2$)$_8$ β-ketoamide) | 295 [M + H]⁺ 293 [M − H]⁻ | δ (CDCl$_3$) = 0.88 (ψ-t, J≈7Hz, 1H, 12-H), 1.20-1.37 (m, 12H, 6-H, 7-H, 8-H, 9-H, 10-H, 11-H), 1.63 (ψ-quint, J=7.3Hz, 2H, 5-H), 2.26 (s, 3H, ring-CH$_3$), 2.56 (t, J=7.3Hz, 2H, 4-H), 3.60 (s, 2H, 2-H), 6.20 (s, 1H, ring-H), 10.16 (s, br., 1H, NH). | + |
| 24 | (3-methylisoxazole amide, (CH$_2$)$_{10}$ β-ketoamide) | 323 [M + H]⁺ 321 [M − H]⁻ | — | + |
| 25 | (4-methyloxazole amide, (CH$_2$)$_5$ β-ketoamide) | 253 [M + H]⁺ 251 [M − H]⁻ | δ (CDCl$_3$) = 0.88 (ψ-t, J≈7Hz, 1H, 9-H), 1.25-1.38 (m, 6H, 6-H, 7-H, 8-H), 1.61 (ψ-quint, J=72Hz, 2H, 5-H), 2.12 (d, J=1.3Hz, 1H, ring-CH$_3$), 2.57 (t, J=7.3Hz, 2H, 4-H), 3.68 (s, br., 2H, 2-H), 7.12 (q, J=1.3Hz, 1H, ring-H), [NH proton not visible]. | + |
| 26 | (4-methyloxazole amide, (CH$_2$)$_8$ β-ketoamide) | 295 [M + H]⁺ 293 [M − H]⁻ | — | + |
| 27 | (4-methyloxazole amide, (CH$_2$)$_{10}$ β-ketoamide) | 323 [M + H]⁺ 321 [M − H]⁻ | — | + |

TABLE 2-continued

Structure and biofilm assay results of the tested compounds.

| # | Compound | HPLC/ MS (ESI) | $^1$H—NMR (300 MHz) | Biofilm inhibition [%]* |
|---|----------|----------------|---------------------|-------------------------|
| 28 | | 278 [M + H]$^+$ 276 [M − H]$^−$ | δ (CDCl$_3$) = 0.87 (ψ-t, J≈7Hz, 1H, 9-H), 1.21-1.37 (m, 6H, 6-H, 7-H, 8-H), 1.59 (ψ-quint, J=7.3Hz, 2H, 5-H), 2.41 (s, 3H, ring-CH$_3$), 2.57 (t, J= 7.3Hz, 2H, 4-H), 3.65 (s, 2H, 2-H), 10.10 (s, br., 1H, NH) | + |
| 29 | | 296 [M + H]$^+$ 294 [M − H]$^−$ | δ (CDCl$_3$) = 0.84 (ψ-t, J≈7Hz, 1H, 9-H), 1.17-1.35 (m, 6H, 6-H, 7-H, 8-H), 1.57 (ψ-quint, J=7.3Hz, 2H, 5-H), 2.55 (t, J=7.3Hz, 2H, 4-H), 3.63 (s, 2H, 2-H), 3.83 (s, 3H, CO$_2$CH$_3$), 6.47 (d, J=3.6Hz, 1H, ring-H), 7.14 (d, J=3.6Hz, 1H, ring-H), 10.15 (s, br., 1H, NH). | + |
| 30 | | 338 [M + H]$^+$ 336 [M − H]$^−$ | — | + |
| 31 | | 366 [M + H]$^+$ 364 [M − H]$^−$ | — | + |
| 32 | | 282 [M + H]$^+$ 280 [M − H]$^−$ | — | +++ |
| 33 | | 296 [M + H]$^+$ 294 [M − H]$^−$ | — | +++ |
| 34 | | 296 [M + H]$^+$ 294 [M − H]$^−$ | — | +++ |
| 35 | | 312 [M + H]$^+$ 310 [M − H]$^−$ | — | +++ |
| 36 | | 326 [M + H]$^+$ 324 [M − H]$^−$ | — | +++ |

TABLE 2-continued

Structure and biofilm assay results of the tested compounds.

| # | Compound | HPLC/MS (ESI) | ¹H—NMR (300 MHz) | Biofilm inhibition [%]* |
|---|---|---|---|---|
| 37 | | 354 [M + H]⁺ 352 [M − H]⁻ | — | + |
| 38 | | 422 [M + H]⁺ 420 [M − H]⁻ | — | +++ |
| 39 | | 381 [M + H]⁺ 379 [M − H]⁻ | — | +++ |
| 40 | | 336 [M + H]⁺ 334 [M − H]⁻ | — | +++ |
| 41 | | 266 [M + H]⁺ 264 [M − H]⁻ | — | + |
| 42 | | 297 [M + H]⁺ 295 [M − H]⁻ | — | + |
| 43 | | 284 [M + H]⁺ 282 [M − H]⁻ | — | +++ |

TABLE 2-continued

Structure and biofilm assay results of the tested compounds.

| # | Compound | HPLC/MS (ESI) | $^1$H—NMR (300 MHz) | Biofilm inhibition [%]* |
|---|---|---|---|---|
| 44 | | 282 [M + H]$^+$ 280 [M − H]$^-$ | — | +++ |
| 45 | | 296 [M + H]$^+$ 294 [M − H]$^-$ | — | + |
| 46 | | 312 [M + H]$^+$ 310 [M − H]$^-$ | — | +++ |
| 47 | | 298 [M + H]$^+$ 296 [M − H]$^-$ | — | +++ |
| 48 | | 312 [M + H]$^+$ 310 [M − H]$^-$ | — | + |
| 49 | | 326 [M + H]$^+$ 324 [M − H]$^-$ | — | + |
| 50 | | 311 [M + H]$^+$ 309 [M − H]$^-$ | — | + |
| 51 | | 284 [M + H]$^+$ 282 [M − H]$^-$ | — | + |

TABLE 2-continued

Structure and biofilm assay results of the tested compounds.

| # | Compound | HPLC/MS (ESI) | ¹H—NMR (300 MHz) | Biofilm inhibition [%]* |
|---|---|---|---|---|
| 52 | | 326 [M + H]⁺ 324 [M − H]⁻ | — | ++ |
| 53 | | 269 [M + H]⁺ 267 [M − H]⁻ | — | + |
| 54 | | 311 [M + H]⁺ 309 [M − H]⁻ | — | + |
| 55 | | 364 [M + H]⁺ 362 [M − H]⁻ | — | + |
| 56 | | 316 [M + H]⁺ 314 [M − H]⁻ | — | + |
| 57 | | 314 [M + H]⁺ 312 [M − H]⁻ | — | + |
| 58 | | 360 [M + H]⁺ 358 [M − H]⁻ | — | + |

TABLE 2-continued

Structure and biofilm assay results of the tested compounds.

| # | Compound | HPLC/MS (ESI) | ¹H—NMR (300 MHz) | Biofilm inhibition [%]* |
|---|---|---|---|---|
| 59 | | 266 [M + H]⁺ 264 [M − H]⁻ | — | +++ |
| 60 | | 294 [M + H]⁺ 292 [M − H]⁻ | — | ++ |
| 61 | | 222 [M + H]⁺ 220 [M − H]⁻ | — | ++ |
| 62 | | 264 [M + H]⁺ 262 [M − H]⁻ | — | ++ |
| 63 | | 366 [M + H]⁺ 364 [M − H]⁻ | — | + |
| 64 | | 262 [M + H]⁺ 260 [M − H]⁻ | — | ++ |
| 65 | | 304 [M + H]⁺ 302 [M − H]⁻ | — | ++ |
| 66 | | 276 [M + H]⁺ 274 [M − H]⁻ | — | + |
| 67 | | 318 [M + H]⁺ 316 [M − H]⁻ | — | + |

TABLE 2-continued

Structure and biofilm assay results of the tested compounds.

| # | Compound | HPLC/ MS (ESI) | $^1$H—NMR (300 MHz) | Biofilm inhibition [%]* |
|---|---|---|---|---|
| 68 | | 278 [M + H]$^+$ 276 [M − H]$^-$ | — | + |
| 69 | | 320 [M + H]$^+$ 318 [M − H]$^-$ | — | ++ |
| 70 | | 292 [M + H]$^+$ 290 [M − H]$^-$ | — | + |
| 71 | | 334 [M + H]$^+$ 332 [M − H]$^-$ | — | + |
| 72 | | 306 [M + H]$^+$ 304 [M − H]$^-$ | — | + |
| 73 | | 348 [M + H]$^+$ 346 [M − H]$^-$ | — | ++ |
| 74 | | 362 [M + H]$^+$ 360 [M − H]$^-$ | — | + |
| 75 | | 318 [M + H]$^+$ 316 [M − H]$^-$ | — | + |

TABLE 2-continued
Structure and biofilm assay results of the tested compounds.
| # | Compound | HPLC/MS (ESI) | $^1$H—NMR (300 MHz) | Biofilm inhibition [%]* |
|---|---|---|---|---|
| 76 | 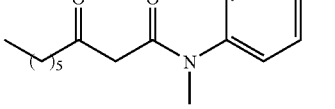 | 296 [M + H]$^+$ 294 [M − H]$^-$ | — | ++ |
| 77 | 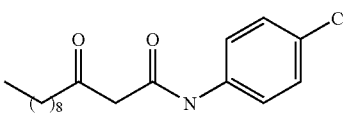 | 338 [M + H]$^+$ 336 [M − H]$^-$ | — | ++ |
| 78 | 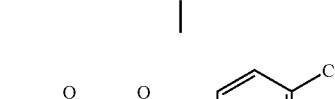 | 366 [M + H]$^+$ 364 [M − H]$^-$ | — | ++ |
| 79 | 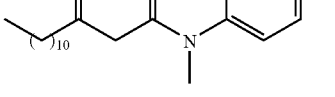 | 280 [M + H]$^+$ 278 [M − H]$^-$ | — | ++ |
| 80 | 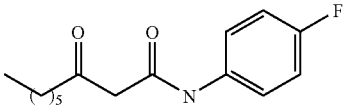 | 322 [M + H]$^+$ 320 [M − H]$^-$ | — | ++ |
| 81 | 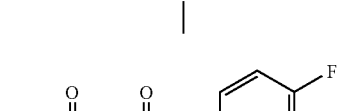 | 330 [M + H]$^+$ 328 [M − H]$^-$ | — | + |
| 82 | 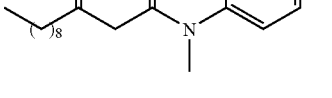 | 372 [M + H]$^+$ 370 [M − H]$^-$ | — | + |
| 83 | 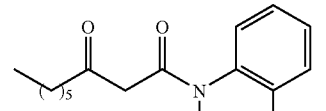 | 340 [M + H]$^+$ 338 [M − H]$^-$ | — | ++ |
| 84 |  | 382 [M + H]$^+$ 380 [M − H]$^-$ | — | + |

TABLE 2-continued

Structure and biofilm assay results of the tested compounds.

| # | Compound | HPLC/MS (ESI) | ¹H—NMR (300 MHz) | Biofilm inhibition [%]* |
|---|---|---|---|---|
| 85 | | 269 [M + H]⁺ 267 [M − H]⁻ | — | + |
| 86 | | 311 [M + H]⁺ 309 [M − H]⁻ | — | + |
| 87 | | 348 [M + H]⁺ 346 [M − H]⁻ | — | + |
| 88 | | 334 [M + H]⁺ 332 [M − H]⁻ | — | +++ |
| 89 | | 308 [M + H]⁺ 306 [M − H]⁻ | — | + |
| 90 | | 358 [M + H]⁺ 356 [M − H]⁻ | — | + |
| 91 | | 304 [M + H]⁺ 302 [M − H]⁻ | — | + |
| 92 | | 320 [M + H]⁺ 318 [M − H]⁻ | — | + |
| 93 | | 368 [M + H]⁺ 366 [M − H]⁻ | — | + |

*+++: 100-60%; ++: 60-30%; +: <30%

2. Inhibition of Biofilm Formation

The bacterial biofilm formation assay was performed in polystyrene microtitre dishes (Greiner Bio-One) according to the method described by O'Toole & Kolter (*Mol. Microbiol.* 28:449-61, 1998) and Pratt & Kolter (*Mol. Microbiol.* 30:285-93, 1998) with few modifications (Huber et al., *Microbiology*, 147:2517-28, 2001). Cells of *Burkholderia cepacia* H111 (Römling et al., *J. Infect. Dis.* 170:1616-21, 1994; Gotschlich et al., *Syst. Appl. Microbiol.* 24:1-14, 2001) were grown in the wells of the microtitre dishes in 100 µl AB medium (Clark & Maaloe, *J. Mol. Biol.* 23:99-112, 1967) supplemented with 10 mM sodium citrate (Sigma). After addition of the test compound (0.5 mM) the cells were incubated for 48 hours at 30° C. The medium was then removed and 100 µl of a 1% (w/v) aqueous solution of crystal violet (Merck) was added. Following staining at room temperature for 20 minutes, the dye was removed and the wells were washed thoroughly with water. For quantification of attached cells, the crystal violet was solubilized in a 80:20 (v/v) mixture of ethanol and acetone and the absorbance was determined at 570 nm (Sunrise, Tecan). Inhibitor-mediated reduction of biofilm formation was correlated with the value obtained without addition of the test compounds. The determined inhibition range (in %) of each compound is listed in Table 2.

To exclude the possibility that the inhibitory effect is attributed to growth inhibition growth curves in the presence and absence of the test compounds were compared. *Burkholderia cepacia* H111 was grown in LB medium at 30° C. in the presence of 0.5 mM test compound. Growth was measured as optical density at 595 nm. None of the compounds listed in Table 2 exhibit any growth inhibitory effects on strain *Burkholderia cepacia* H111.

The invention claimed is:

1. A compound of Formula (XIII), and/or a pharmaceutically acceptable salt, thereof:

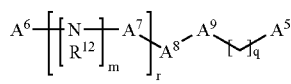

(XIII)

wherein
A$^7$ is independently C=O, C=S, SO$_2$, CH—OR$^{13}$, C=NR$^{12}$, or CH$_2$—CHOR$^{13}$;
A$^8$ is independently C(R$^{14}$)$_2$, O, S, or NR$^{12}$;
A$^9$ is independently C=O, C=S, SO$_2$, CH—OR$^{13}$, C=NR$^{12}$, or CH$_2$—CHOR$^{13}$;
m is 0, or 1;
q is 1;
r is 1;
R$^{12}$ is independently H, CH$_3$, CH$_2$—CH$_3$, C$_6$H$_5$, OCH$_3$, OCH$_2$—CH$_3$, OH, or SH;
R$^{13}$ is independently H, CH$_3$, or CH$_2$—CH$_3$;
R$^{14}$ is independently H, alkyl, alkoxy, OH, or SH;
A$^5$ is an optionally substituted C$_3$-C$_{16}$-alkyl group by one or more substituents R$^3$,
A$^6$ is an optionally substituted thiazole group, which can optionally be substituted by one or more substituents R$^8$, R$^{8'}$, or R$^9$,
R$^8$, R$^{8'}$, R$^9$ is independently methyl, ethyl, t-butyl, CN, halogen, haloalkoxy, haloalkyl, OH, alkoxy, NR$^4$R$^5$, or COOR$^4$;
R$^3$ is independently OR$^4$, SR$^4$, hydroxyalkyl, hydroxyalkylamino, cycloalkyl, halogen, haloalkyl, haloalkyloxy, NO$_2$, CN, SO$_2$NR$^4$R$^5$, CONR$^4$R$^5$, COR$^4$, CO$_2$R$^4$, SO$_2$R$^4$, SO$_3$R$^4$, NR$^4$R$^5$, alkyl, aryl or heteroaryl;
R$^4$ is H, alkyl, cycloalkyl, aryl or heteroaryl; and
R$^5$ is H, O-alkyl, O-aryl, alkyl, heteroaryl or aryl.

2. The compound according to claim 1 wherein A$^5$ is an optionally substituted C$_6$-C$_{11}$ alkyl group.

3. The compound according to claim 1 wherein A$^8$ is CH$_2$.

4. The compound according to claim 1 wherein A$^7$ is C=O and A$^9$ is C=O.

5. The compound according to claim 1 wherein m is 1, A$^7$ is C=O, A$^9$ is C=O, A$^8$ is CH$_2$, R$^{12}$ is H, and A$^5$ is an optionally substituted C$_6$-C$_{11}$ alkyl group.

6. A pharmaceutical composition comprising a compound according to claim 1, and/or a pharmaceutically acceptable salt thereof and a pharmaceutically acceptable diluent or carrier.

7. The compound according to claim 1, wherein A$^6$ is 1,3-thiazole.

8. A compound, and/or a pharmaceutically acceptable salt thereof, selected from the group consisting of

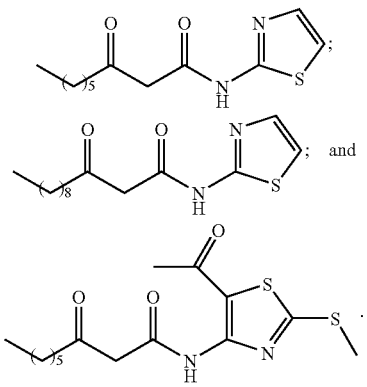

* * * * *